US011452761B2

(12) United States Patent
Sakamoto et al.

(10) Patent No.: US 11,452,761 B2
(45) Date of Patent: Sep. 27, 2022

(54) METHOD FOR INHIBITING RENAL HYPOFUNCTION IN NON-HUMAN ANIMAL

(71) Applicant: KANEKA CORPORATION, Osaka (JP)

(72) Inventors: Hirokazu Sakamoto, Hyogo (JP); Hiroetsu Suzuki, Tokyo (JP); Kentaro Katayama, Tokyo (JP); Yuki Tochigi, Tokyo (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 16/239,806

(22) Filed: Jan. 4, 2019

(65) Prior Publication Data

US 2019/0117731 A1 Apr. 25, 2019

Related U.S. Application Data

(63) Continuation of application No. PCT/JP2017/024468, filed on Jul. 4, 2017.

(30) Foreign Application Priority Data

Jul. 4, 2016 (JP) .............................. JP2016-132757

(51) Int. Cl.
| | | |
|---|---|---|
| *A61K 38/18* | (2006.01) | |
| *A61K 47/10* | (2017.01) | |
| *C07K 14/505* | (2006.01) | |
| *C07K 1/107* | (2006.01) | |
| *A61P 13/12* | (2006.01) | |
| *A61K 38/17* | (2006.01) | |
| *A61K 47/60* | (2017.01) | |
| *A61K 45/06* | (2006.01) | |

(52) U.S. Cl.
CPC .......... *A61K 38/1816* (2013.01); *A61K 38/17* (2013.01); *A61K 45/06* (2013.01); *A61K 47/10* (2013.01); *A61K 47/60* (2017.08); *A61P 13/12* (2018.01); *C07K 1/107* (2013.01); *C07K 14/505* (2013.01)

(58) Field of Classification Search
None
See application file for complete search history.

(56) References Cited

U.S. PATENT DOCUMENTS

| | | | | |
|---|---|---|---|---|
| 7,309,687 | B1 * | 12/2007 | Brines ................. | A61K 38/1816 514/15.1 |
| 2006/0172389 | A1 * | 8/2006 | MacLeod ............. | C07K 14/505 435/69.1 |
| 2007/0275882 | A1 * | 11/2007 | Meijer ................... | A61P 13/12 530/397 |
| 2008/0146543 | A1 * | 6/2008 | Stark ....................... | A61P 9/00 514/212.07 |
| 2009/0158449 | A1 * | 6/2009 | Nakaishi ............. | A01K 67/0275 800/5 |
| 2010/0093608 | A1 * | 4/2010 | Tian ...................... | C07K 14/505 514/1.1 |
| 2012/0264687 | A1 | 10/2012 | Tani et al. | |
| 2016/0083444 | A1 * | 3/2016 | Lu ........................ | C07K 14/505 424/134.1 |
| 2016/0353717 | A1 | 12/2016 | Nakaishi et al. | |

FOREIGN PATENT DOCUMENTS

| | | | |
|---|---|---|---|
| JP | 200789578 | A | 4/2007 |
| JP | 2008-536935 | A | 9/2008 |
| JP | 2010111595 | A | 5/2010 |
| JP | 2012504136 | A | 2/2012 |
| WO | WO-2006055973 | A2 * | 5/2006 ......... A61K 38/1816 |
| WO | 2006/113752 | A1 | 10/2006 |
| WO | 2011034105 | A1 | 3/2011 |

OTHER PUBLICATIONS

Geddes et al. Fibroblast growth factor 23 in feline chronic kidney disease. Abstract. Journal of Veterinary Internal Medicine , vol. 27, No. 2, pp. 234-241 (2013). (Year: 2013).*
Bhattacharya et al. Impact of genetic variation on three dimensional structure and function of proteins; PLOS One 12(3): e0171355, pp. 1-22 (Mar. 2017). (Year: 2017).*
Tokuriki et al., Stability effects of mutations and protein evolvability; Current Opinion in Structural Biology, 19:596-604 (2009). (Year: 2009).*
Gross et al. Cellular Trafficking and Degradation of Erythropoietin and Novel Erythropoiesis Stimulating Protein (NESP). The Journal of Biological Chemistry, vol. 281, No. 4:2024-2032 (2006). (Year: 2006).*
Rosse et al. Factors Controlling Erythropoiesis in Birds. Blood vol. 27/No. 5, pp. 654-661 (May 1966). (Year: 1966).*
Yap et al. Effects of experimental manipulation of hematocrit on avian flight performance in high-and low-altitude conditions. Journal of Experimental Biology vol. 221, No. Pt 22, pp. 1-10 (Nov. 14, 2018). (Year: 2018).*
Wen et al. Erythropoietin Structure-Function Relationships: High Degree of Sequence Homology Among Mammals. Blood, vol. 82, No. 5 pp. 1507-1516; (Sep. 1, 1993). (Year: 1993).*

(Continued)

*Primary Examiner* — Elizabeth C. Kemmerer
*Assistant Examiner* — Regina M DeBerry
(74) *Attorney, Agent, or Firm* — Osha Bergman Watanabe & Burton LLP

(57) ABSTRACT

A method for inhibiting renal hypofunction in a non-human animal includes administering cat-derived erythropoietin to the non-human animal. The non-human animal may have renal hypofunction. The non-human animal may have chronic kidney disease and the renal hypofunction may be caused by the chronic kidney disease. The cat-derived erythropoietin may be administered repeatedly at a time interval of 7 to 30 days.

13 Claims, 7 Drawing Sheets
Specification includes a Sequence Listing.

(56) References Cited

OTHER PUBLICATIONS

Yamaleyeva et al., "Cell Therapy with Human Renal Cell Cultures Containing Erythropoietin-Positive Cells Improves Chronic Kidney Injury," Stem Cells Translational Medicine, 2012, vol. 1, p. 373-383 (11 pages).
International Search Report issued in corresponding International Application No. PCT/JP2017/024468; dated Aug. 3, 2017 (2 pages).
International Preliminary Report on Patentability issued in corresponding International Application No. PCT/JP2017/024468; dated Jan. 8, 2019 (5 pages).
Y. Miyagawa, "Kidneys (Chronic kidney disease) of elderly dogs and cats" Journal of Modern Veterinary Medicine, Apr. 2016, Extra edition, No. 161, pp. 27-39 (22 pages).
Office Action issued in Japanese Application No. 2016-132757, dated May 12, 2020 (6 pages).
Randolph et al., "Expression, bioactivity, and clinical assessment of recombinant feline erythropoietin"; American Journal of Veterinary Research, American Veterinary Medicine Association; vol. 65, No. 10; Oct. 1, 2004; p. 1355-1366 (12 pages).
Roudebush et al., "Therapies for feline chronic kidney disease"; Journal of Feline Medicine and Surgery; vol. 11, No. 3; Mar. 1, 2009; p. 195-210 (16 pages).
Extended European Search Report issued in corresponding European Application No. 17824229.3, dated Feb. 19, 2020 (8 pages).

\* cited by examiner

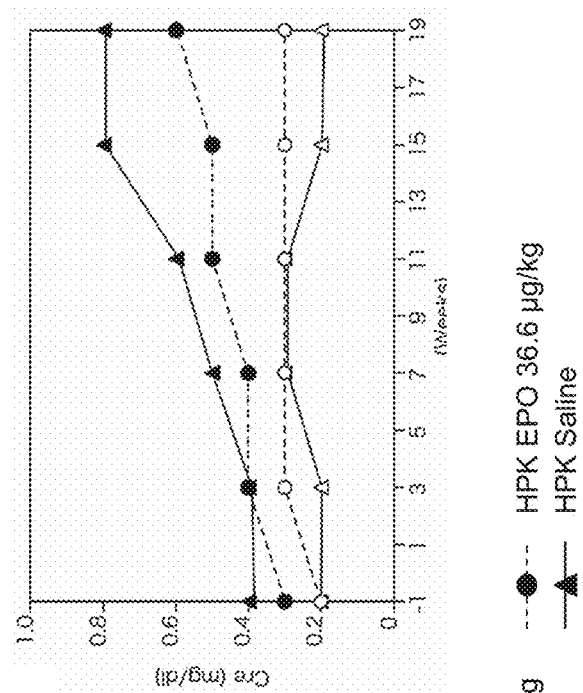
Fig. 2G
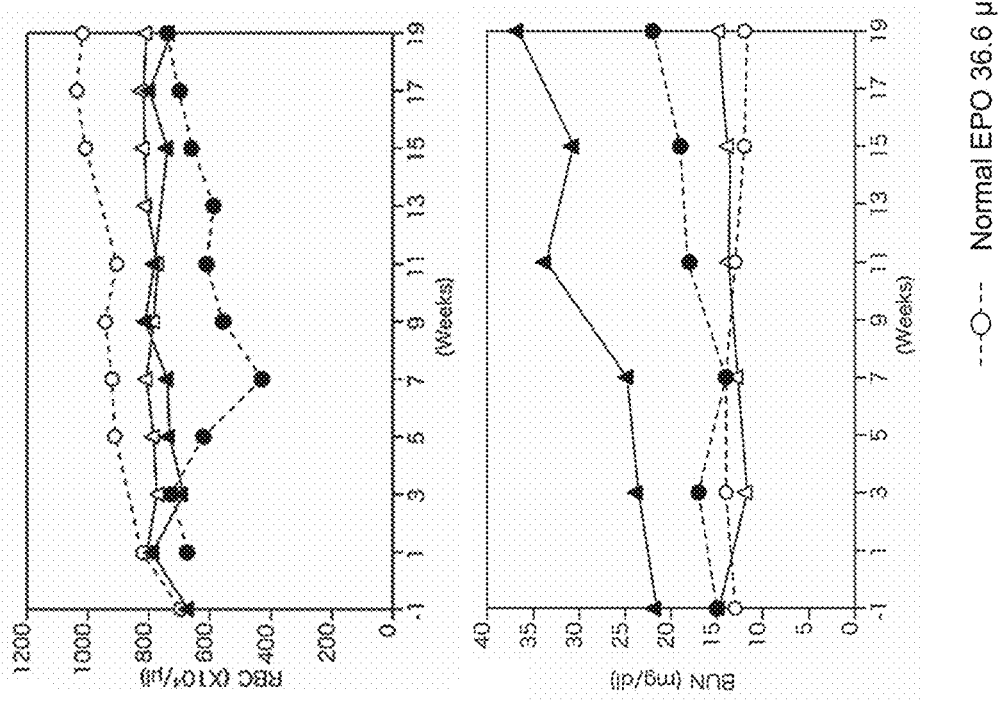
Fig. 2E
Fig. 2F

METHOD FOR INHIBITING RENAL HYPOFUNCTION IN NON-HUMAN ANIMAL

TECHNICAL FIELD

One or more embodiments of the present invention relate to a method for inhibiting renal hypofunction in a non-human animal.

One or more embodiments of the present invention relate to a medicament for non-human animal use for inhibiting renal hypofunction in a non-human animal.

BACKGROUND

Cats are animals to which humans have always felt an attachment as pets, and are now establishing themselves as a member of the human society as "companion animals". Meanwhile, cats have heretofore been used as laboratory animals, for example, in the medical, pharmaceutical, veterinary, and psychological fields, and also used in safety or effect tests for pharmaceuticals. In these circumstances involving the increasing social importance of cats, feline diseases or infectious diseases are of great concern, and effective treatment methods therefor are demanded. In recent years, pharmaceutical proteins have also attracted attention for the treatment of feline diseases. Typically, pharmaceutical proteins for human use are diverted thereto. However, the pharmaceutical proteins for human use differ in amino acid sequence from in vivo proteins originally carried by cats and might therefore produce different effects in vivo. Furthermore, such difference in amino acid sequence might cause allergy as a result of recognition as foreign matter, or worse, causes anaphylaxis-like symptoms.

The present applicant produced cat-derived erythropoietin (fEPO), which is a pharmaceutical protein for cat, by using transgenic birds and used the fEPO in the treatment of diseases such as renal anemia in cats (Patent Literatures 1 and 2).

Meanwhile, chronic kidney disease (CKD) is a disease concept proposed for the first time in Kinney Disease Outcomes Quality Initiative (K/DOQI) issued in 2001 by the National Kidney Foundation (NIKE) as to humans (Non Patent Literature 1). CKD is a broad concept including early renal hypofunction conditions to even the terminal stage of renal failure. The concept of CKD has also been introduced in veterinary medicine. In Non Patent Literature 2, CKD is defined as a disease that satisfies at least one of (1) kidney damage (demonstrated from tissues, blood, urinalysis or diagnostic imaging) that has been present for at least 3 months, and (2) reduction in glomerular filtration rate (GFR) (50% or more reduction in GFR from the normal level) that has been present for at least 3 months (Non Patent Literatures 1 and 2). The international Renal Interest Society (IRIS) has announced the IRIS staging system which classifies CKD in non-human animals into stages I to IV (Non Patent Literatures 1, 3, and 4).

EPO is a hormone that has an effect of regulating the production of red blood cells. Specifically, EPO acts on erythroid progenitors to differentiate the erythroid progenitors into red blood cells. Renal anemia develops by reduction of red blood cells resulting from the decreased amount of EPO in the kidney at a stage of renal failure, which is a stage advanced from renal hypofunction. In addition, various causes are possible as causes of renal anemia. For example, deterioration in nutritional status by long-term loss of appetite ascribable to chronic kidney disease is also considered as one of the causes of renal anemia. It is further known that at the uremic stage, the life span of red blood cells is shortened by the influence of uremic toxin, encouraging anemia. Reportedly, in azotemia, poikilocytes or schistocytes tend to appear, and also, hemolysis tends to occur. A method for treating renal anemia, comprising stimulating the production of red blood cells by administering cat-derived EPO to a non-human animal with renal anemia has previously been disclosed in Patent Literature 3, etc. Renal anemia is a symptom that appears at the late stage of CKD based on the IRIS staging (stage III or stage IV). For example, in Example 33 of Patent Literature 3, cat-derived EPO was administered in order to treat anemia in cats having CKD of stage III or stage IV.

CITATION LIST

Patent Literature

Patent Literature 1: JP Patent Publication (Kokai) No. 2007-89578 A (2007)
Patent Literature 2: JP Patent Publication (Kokai) No. 2010-111595 A (2010)
Patent Literature 3: JP Patent Publication (Kohyo) No. 2012-504136 A (2012)

Non Patent Literature

Non Patent Literature 1: Yasuto Kuwahara, Journal of Animal Clinical Medicine, 20 (3), 71-75, 2011
Non Patent Literature 2: Polzin D J, et al., Chronic kidney disease. In the Textbook of Veterinary Internal Medicine 6th ed, Ettinger S J & Feldman E C eds, 1756, W. B. Saunders, Philadelphia (2005)
Non Patent Literature 3: Jonathan Elliott and Gregory F Grauer ed., "BSAVIA Manual of Canine and Feline Nephrology and Urology-II", p. 155-162, New LLL Publisher
Non Patent Literature 4: Website of International Renal Interest Society (IRIS)

The conventional treatment of renal anemia in non-human animals with EPO involves administering EPO, which has an insufficient level in animals with CKD, thereby elevating the amount of EPO in the body and promoting red blood cell production. This treatment merely replaces the already reduced ability of the kidney to produce EPO with the administration of EPO and does not inhibit renal hypofunction.

At the early stage of CKD (e.g., stage I or stage II based on the IRIS staging), the EPO production function of the kidney still remains sufficiently. At this stage, it is important to inhibit the progression of CKD by inhibiting renal hypofunction, rather than to compensate for the shortage of EPO. However, any satisfiable approach for inhibiting renal hypofunction in non-human animals has not yet been provided.

SUMMARY

One or more embodiments of the present invention provide an approach for inhibiting renal hypofunction in a non-human animal.

The present specification discloses the following as one or more embodiments of the present invention.
(1) A method for inhibiting renal hypofunction in a non-human animal, the method comprising
a step of administering cat-derived erythropoietin to the non-human animal.

(2) The method according to (1), wherein the renal hypofunction is caused by chronic kidney disease.
(3) The method according to (1) or (2), wherein the administration step is a step of administering the erythropoietin to the animal at a time interval of a period of 7 days or longer and 30 days or shorter.
(4) The method according to (3), wherein the dose of the erythropoietin per the period is 3 μg/kg body weight or larger and 400 μg/kg body weight or smaller.
(5) The method according to any of (1) to (4), wherein the animal is a non-human animal having or suspected of having chronic kidney disease without anemia at least at the start of the administration step.
(6) The method according to any of (1) to (5), wherein the animal is a non-human animal having or suspected of having chronic kidney disease classified into chronic kidney disease stage I or stage II defined by the International Renal Interest Society at least at the start of the administration step.
(7) The method according to any of (1) to (6), wherein the creatinine concentration in blood of the animal is 17 mg/dL or lower at least at the start of the administration step.
(8) The method according to any of (1) to (7), further comprising at least one step selected from the group consisting of taking iron supplementation, administering intravenous fluids, performing dialysis, performing diet therapy, administering an antihypertensive agent, administering an adsorbent, administering vitamin, and administering a diuretic.
(9) A medicament for non-human animal use for inhibiting renal hypofunction in a non-human animal, the medicament comprising cat-derived erythropoietin.
(10) The medicament for non-human animal use according to (9), wherein the renal hypofunction is caused by chronic kidney disease.
(11) The medicament for non-human animal use according to (9) or (10), wherein the medicament is for administering the erythropoietin to the animal at a time interval of a period of 7 days or longer and 30 days or shorter.
(12) The medicament for non-human animal use according to (11), wherein the medicament is for administering the erythropoietin at a dose of 3 μg/kg body weight or larger and 400 μg/kg body weight or smaller per the period.
(13) The medicament for non-human animal use according to any of (9) to (12), wherein the medicament is for administration to a non-human animal having or suspected of having chronic kidney disease without anemia at least at the start of the administration.
(14) The medicament for non-human animal use according to any of (9) to (13), wherein the medicament is for administration to a non-human animal having or suspected of having chronic kidney disease classified into chronic kidney disease stage I or stage II defined by the International Renal Interest Society at least at the start of the administration.
(15) The medicament for non-human animal use according to any of (9) to (14), wherein the medicament is for administration to a non-human animal having a creatinine concentration in blood of 2.7 mg/dL or lower at least at the start of the administration.
(16) Use of cat-derived erythropoietin in the manufacture of a medicament for non-human animal use for inhibiting renal hypofunction in a non-human animal.
(17) The use according to (16), wherein the medicament for non-human animal use is a medicament for non-human animal use that is for use in a method according to any of (1) to (8).
(18) Cat-derived erythropoietin for inhibiting renal hypofunction in a non-human animal.
(19) The cat-derived erythropoietin according to (18), wherein the renal hypofunction is caused by chronic kidney disease.
(20) The cat-derived erythropoietin according to (18) or (19), wherein the cat-derived erythropoietin is for administration to the animal at a time interval of a period of 7 days or longer and 30 days or shorter.
(21) The cat-derived erythropoietin according to (20), wherein the cat-derived erythropoietin is for administration at a dose of 3 μg/kg body weight or larger and 400 μg/kg body weight or smaller per the period.
(22) The cat-derived erythropoietin according to any of (18) to (21), wherein the cat-derived erythropoietin is for administration to a non-human animal having or suspected of having chronic kidney disease without anemia at least at the start of the administration.
(23) The cat-derived erythropoietin according to any of (18) to (22), wherein the cat-derived erythropoietin is for administration to a non-human animal having or suspected of having chronic kidney disease classified into chronic kidney disease stage I or stage II defined by the International Renal Interest Society at least at the start of the administration.
(24) The cat-derived erythropoietin according to any of (18) to (23), wherein the cat-derived erythropoietin is for administration to a non-human animal having a creatinine concentration in blood of 2.7 mg/dL or lower at least at the start of the administration.
(25) Cat-derived erythropoietin for inhibiting renal hypofunction in a non-human animal by a method according to any of (1) to (8).

The present application claims the priority of Japanese Patent Application No. 2016-132757, the content of which is incorporated herein.

The method according to one or more embodiments of the present invention is capable of inhibiting renal hypofunction in a non-human animal.

BRIEF DESCRIPTION OF DRAWINGS

FIG. 2A shows data for body weight, FIG. 2B shows data for food intake, FIG. 2C shows data for water intake, and FIG. 2D shows data for urine weight. The food intake, the water intake, and the urine weight are indicated by values corrected with the body weight (B.W.). Each graph shows values on an individual basis.

FIGS. 2E to 2G are graphs showing change in blood cell component and plasma component of an animal in the experimental period in Test 1. FIG. 2E shows data for red blood cell (RBC), FIG. 2F shows data for blood urea nitrogen (BUN), and FIG. 2G shows data for creatinine (Cre) concentration. Each graph shows values on an individual basis.

DETAILED DESCRIPTION OF EMBODIMENTS

<Cat-Derived Erythropoietin>

Figure 1:
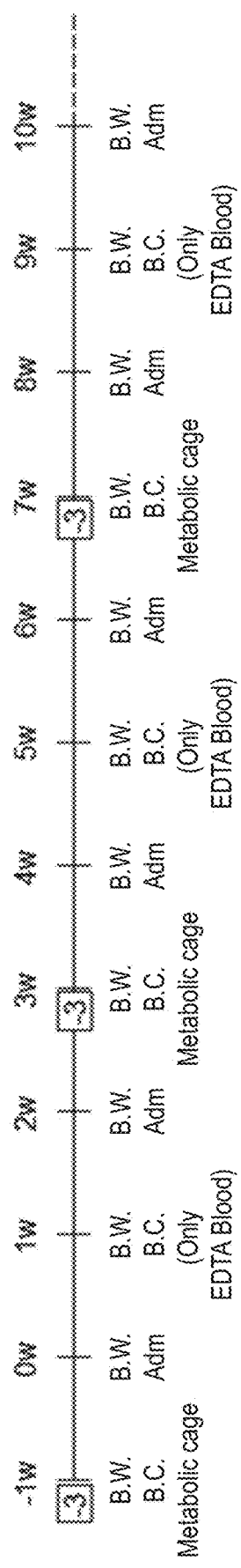
FIG. 1 is a diagram for illustrating an experimental schedule in Test 1 and Test 2.

Hereinafter, erythropoietin is also referred to as "EPO". Cat-derived erythropoietin or feline erythropoietin is also referred to as "fEPO".

The nucleotide sequence of DNA encoding fEPO is shown in SEQ ID NO: 1. An amino acid sequence encoded by the nucleotide sequence represented by SEQ ID NO: 1 is as shown in SEQ ID NO: 2. The protein having the amino acid sequence shown in SEQ ID NO: 2 is called "fEPO preprotein", because the 1st to 26th amino acid residues in this amino acid sequence is a signal sequence. An amino acid sequence that is derived from the fEPO preprotein by the removal of the signal sequence and the deletion of the 192nd amino acid residue is of mature fEPO. The amino acid sequence of the mature fEPO is as shown in SEQ ID NO: 3. The fEPO may be a polypeptide partially comprising the amino acid sequence of the fEPO preprotein represented by SEQ ID NO: 2, or a polypeptide partially comprising the amino acid sequence of the mature fEPO represented by SEQ ID NO: 3.

The fEPO is not limited to the fEPO preprotein consisting of the amino acid sequence represented by SEQ ID NO: 2 and the mature fEPO consisting of the amino acid sequence represented by SEQ ID NO: 3, and an active mutant thereof can also be used. The active mutant is preferably a polypeptide that exhibits activity of 10% or more, preferably 40% or more, more preferably 60% or more, further preferably 80% more of that in the case of using the fEPO preprotein consisting of the amino acid sequence represented by SEQ ID NO: 2 or the mature fEPO consisting of the amino acid sequence represented by SEQ ID NO: 3 under activity measurement conditions shown in Examples of the present specification. The active mutant described above corresponds to, for example, a polypeptide consisting of an amino acid sequence derived from the amino acid sequence represented by SEQ ID NO: 2 or 3 by the addition, deletion, or substitution of one to several amino acids, more preferably a polypeptide consisting of an amino acid sequence derived from the amino acid sequence represented by SEQ ID NO: 2 or 3 by the N-terminal and/or C-terminal addition, deletion, or substitution of one to several amino acids in total, or a polypeptide consisting of an amino acid sequence having 80% or more, preferably 85% or more, more preferably 90% or more, 95% or more, 97% or more, 98% or more or 99% or more amino acid identity to the amino acid sequence represented by SEQ ID NO: 2 or 3. The active mutant of the fEPO preprotein consisting of the amino acid sequence represented by SEQ ID NO: 2 more preferably contains the mutation as described above at at least one site selected from the N terminus, the C terminus, a moiety from the 1st to 26th residues and the 192nd residue of SEQ ID NO: 2. A methionine residue encoded by a start codon may be added to the N terminus of the mature fEPO consisting of the amino acid sequence represented by SEQ ID NO: 3. In the present specification, the term "several" refers to, for example, 2 or more, 3 or more, 4 or more, 5 or more, 6 or more, 7 or more, 8 or more, 9 or more, or 10 or more, and 50 or less, 45 or less, 40 or less, 35 or less, 30 or less, 29 or less, 28 or less, 27 or less, 26 or less, 25 or less, 24 or less, 23 or less, 22 or less, 21 or less, 20 or less, 19 or less, 18 or less, 17 or less, 16 or less, 15 or less, 14 or less, 13 or less, 12 or less, or 11 or less. The "amino acid identity" refers to the ratio (%) of identical amino acid residues to the total number of amino acid residues of the protein shown in SEQ ID NO: 2 or 3 when two amino acid sequences are aligned with a gap introduced, if necessary, so as to attain the highest degree of amino acid consistency therebetween. The amino acid identity can be calculated using a protein search system provided by BLAST or FASTA (Karlin, S. et al., 1993, Proc. Natl. Acad. Sci. USA, 90: 5873-5877; Altschul, S. F. et al., 1990, J. Mol. Biol., 215: 403-410; and Pearson, W. R. et al., 1988, Proc. Natl. Acad. Sci. USA, 85: 2444-2448). The amino acid substitution is desirably conservative amino acid substitution. The "conservative amino acid substitution" refers to the substitution between amino acids similar in nature such as charge, side chain, polarity, or aromaticity. The amino acids similar in nature can be classified into, for example, basic amino acids (arginine, lysine, and histidine), acidic amino acids (aspartic acid and glutamic acid), uncharged polar amino acids (glycine, asparagine, glutamine, serine, threonine, cysteine, and tyrosine), apolar amino acids (leucine, isoleucine, alanine, valine, proline, phenylalanine, tryptophan, and methionine), branched amino acids (leucine, valine, and isoleucine), and aromatic amino acids (phenylalanine, tyrosine, tryptophan, and histidine).

For example, fEPO produced in a transgenic cell genetically modified to express fEPO by the transfer of a foreign gene encoding fEPO to a generally available animal cell (e.g., a CHO cell), plant cell, prokaryote, or yeast as a host, fEPO produced in a transgenic animal or a transgenic plant genetically modified to express fEPO by the transfer of a foreign gene encoding fEPO, or fEPO produced using a cell-free protein synthesis system can be utilized, though the fEPO according to one or more embodiments of the present invention is not limited thereto. Examples of the transgenic animal include birds. The birds are preferably domesticated birds such as chickens, quails, turkeys, ducks, domestic ducks, ostriches, gooses, long-tailed cocks, bantams, pigeons, emus, pheasants, and guinea fowls, particularly preferably chickens. The transgenic birds preferably accumulate fEPO in eggs. The method for producing transgenic birds expressing fEPO in eggs and obtaining the fEPO from the eggs is as described in Patent Literature 1, etc. The transgenic plant is not particularly limited and may be a monocot or a dicot. Examples of the monocot include, but are not limited to, plants belonging to the family. Poaceae (rice, barley, wheat, corn, sugarcane, turf, sorghum, foxtail millet, Japanese millet, etc.), the family Liliaceae (asparagus, lily, onion, Chinese leek, Japanese dog's tooth violet, etc.), and the family Zingiberaceae (ginger, Japanese ginger, turmeric, etc.). Examples of the dicot include, but are not limited to, plants belonging to the family Brassicaceae (thale-cress, cabbage, rapeseed, cauliflower, broccoli, daikon radish, etc.), the family Solanaceae (tomato, eggplant, potato, tobacco, etc.), the family Leguminosae (soybean, pea, common bean, alfalfa, etc.), the family Cucurbitaceae (cucumber, melon, pumpkin, etc.), the family Umbelliferae (carrot, celery, Japanese honewort, etc.), the family Compositae (lettuce, etc.), the family Malvaceae (cotton, okra, etc.), the family Chenopodiaceae (sugarbeet, spinach, etc.), the family Myrtaceae (eucalyptus, clove, etc.), and the family Salicaceae (poplar, etc.).

The fEPO polypeptide may be modified with one or more sugar chains or other groups. The type and the number of the sugar chain to modify the fEPO are not particularly limited, and the fEPO is generally modified with the type and the number of the sugar chain according to the expression system used (i.e., a transgenic cell, a transgenic animal, a transgenic plant, a cell-free protein synthesis system, etc.). When the expression system used is, for example, a chicken, the sugar chain modification is typically modification with a sugar chain in which 2 to 5 sugar chains containing a β-N-acetylglucosamine residue are bonded to a trimannosyl core.

The fEPO used in one or more embodiments of the present invention may be chemically modified with a water-soluble long-chain molecule. The water-soluble long-chain molecule is not particularly limited, and may be, for example, PEG (polyethylene glycol), polyamino acid, or polypropylene glycol. The water-soluble long-chain molecule can be added to the protein through synthesis reaction by preparing a reaction precursor. Among these water-soluble long-chain molecules, PEG has neither antigenicity nor toxicity and is therefore also effective in view of reducing the antigenicity of the modified protein and suppressing the expression of an anti-protein antibody as an adverse reaction.

The life span in blood of the water-soluble long-chain molecule-fEPO conjugate is increased with increase in the molecular weight of the water-soluble long-chain molecule, such as PEG, to be added. However, the addition of a very high-molecular-weight water-soluble long-chain molecule inhibits the hematopoietic activity of fEPO (WO02/032957). Hence, the weight-average molecular weight of the water-soluble long-chain molecule is preferably 5 kDa or larger and 40 kDa or smaller for maximizing an in vivo hematopoietic effect, more preferably 10 kDa or larger and 30 kDa or smaller, further preferably 20 kDa.

The fEPO has at least 3 sites to which the water-soluble long-chain molecule can be bonded. Accordingly 1 (mono), 2 (di), or 3 (tri) molecules of the water-soluble long-chain molecule can bind to one molecule of fEPO polypeptide. The bonding of PEG to a plurality of sites may inhibit the ability of the EPO to bind to a receptor and reduces its in vivo activity. Hence, a mono-PEGylated fEPO or a di-PEGylated fEPO is preferred, and a di-PEGylated fEPO is particularly preferred.

In one or more embodiments of the present invention, the "chemical modification" refers to a chemical alteration of a particular functional group of the fEPO to change functions such as activity or reactivity. The chemical modification of the fEPO with the water-soluble long-chain molecule such as PEG includes addition of the water-soluble long-chain molecule to the polypeptide constituting the fEPO by forming a covalent bond through a reaction of a functional group (e.g., a primary amino group) carried by the polypeptide constituting the fEPO with a functional group carried by the water-soluble long-chain molecule.

Examples of the method for chemically modifying the fEPO with the water-soluble long-chain molecule include an approach which involves mixing the fEPO and the water-soluble long-chain molecule at a molar ratio of approximately 1:1 to 10, then reacting the mixture for 30 to 180 minutes with mixing at 4 to 37° C., adding thereto a 100 mM glycine solution as a reaction terminator in an amount of approximately ⅒, and terminating the reaction with mixing at 4 to 37° C. for 1 hour.

The water-soluble long-chain molecule-modified fEPO preferably has the number of addition of the water-soluble long-chain molecule of 1 or more and an apparent molecular weight of 100 kDa to 900 kDa in an aqueous solvent measured by the gel filtration column chromatography of one molecule modified with the water-soluble long-chain molecule, more preferably the number of addition of the water-soluble long-chain molecule of 1 and the apparent molecular weight of 100 kDa to 500 kDa, or the number of addition of the water-soluble long-chain molecule of 2 and the apparent molecular weight of 100 kDa to 500 kDa. The measurement of the apparent molecular weight by the gel filtration column chromatography is performed using a low-pressure chromatography apparatus AKTA explorer 100 (manufactured by Amersham plc) and a gel filtration column Superdex 200 10/300 (manufactured by Amersham plc).

A general method for covalently bonding a water-soluble long-chain molecule to a protein may employ a chemical reaction involving an oxidatively activatable functional group, such as polyol, lactol, amine, carboxylic acid or carboxylic acid derivative, carried by a protein or a sugar chain. An alternative method may employ a sulfonate ester-activated polymer, for example, sulfonate ester-activated PEG. These methods may be used for adding a water-soluble long-chain molecule to EPO.

Hereinafter, a preferred embodiment employing PEG as a water-soluble long-chain polymer will be described.

A long-chain molecule methoxylated at one end can be used as a PEGylation reaction precursor for covalently bonding PEG to the protein. Engineered PEG has been developed in which the non-methoxylated end has been further altered to a group capable of forming a covalent bond in response to nucleophilic reaction with a nucleophilic group, such as an amino group, carried by fEPO (e.g., succinimidyl fatty acid-esterified PEG). Among others, a PEGylation reaction precursor represented by the following formula:

$$CH_3-O-(CH_2CH_2O)_n-X-Y$$

wherein

Y represents a leaving group such as a succinimidyloxy group,

X represents a group represented by $-(CH_2)_m-C(=O)-$ m is an integer of 1 or larger and 8 or smaller, more preferably 4 or larger and 6 or smaller, most preferably 5, and n is an integer representing the degree of polymerization is preferred in view of reactivity.

It is known that the PEGylation reaction precursor represented by the formula is selectively added to the amino group of an N-terminal amino acid, or a lysine residue through reaction with human EPO. EPO has a plurality of lysine residues. Hence, as the reaction proceeds, the number of addition of PEG is increased, resulting in a mixture of isomers differing in the number of addition. For the fEPO consisting of the amino acid sequence of SEQ ID NO: 2, it is preferred to PEGylate alanine 27, lysine 71 and/or lysine 78. For the mature fEPO consisting of the amino acid sequence of SEQ ID NO: 3, it is preferred to PEGylate alanine 1, lysine 45 and/or lysine 52.

In one or more embodiments of the present invention, the term "cat-derived erythropoietin", "feline EPO", or "fEPO" also encompasses the chemically modified cat-derived erythropoietin as mentioned above and conceptually encompasses cat-derived erythropoietin in various forms such as the mature fEPO and the fEPO preprotein as described above, unless otherwise specified. If it is particularly necessary to point out explicitly the PEGylated form of the cat-derived erythropoietin, this form may be described as the "PEGylated fEPO". The same holds true for the case of defining other forms.

The fEPO prepared using the expression system as described above and chemically modified, if necessary, can be purified and recovered using, alone or in combination, general protein purification approaches, such as salting-out, adsorption column chromatography, ion-exchange column chromatography, size exclusion chromatography, and antibody column technique, though the purification method for fEPO is not limited thereto. Examples of the adsorption column chromatography include Blue Sepharose chromatography and heparin chromatography. Examples of the ion-exchange column chromatography include cation-exchange chromatography and anion-exchange chromatography. It is preferred to use purified fEPO from which impurities such as other proteins have been removed to an extent acceptable as a pharmaceutical for non-human animal use.

The fEPO used in one or more embodiments of the present invention can be in a form that can be administered through various administration routes mentioned later to a non-human animal, and may be in any form. The fEPO is preferably in the form of a composition for administration to a non-human animal, comprising the fEPO in combination with an additional component acceptable for the administration to a non-human animal.

<Non-Human Animal Serving as Subject>

The "non-human animal" serving as a subject for the method for inhibiting renal hypofunction and the method for inhibiting chronic kidney disease according to one or more embodiments of the present invention can be an animal other than humans and is not particularly limited. A non-human mammal is preferred. Examples of the non-human mammal include: companion animals or laboratory animals such as dogs, cats, and rodents (rats and mice); livestock animals such as cattle, horses, sheep, goat, and pigs; and lions, tigers, elephants, giraffes, zebras, koalas, and pandas raised or exhibited in zoos, etc. The non-human animal is particularly preferably a mammal belonging to the order Carnivora. Examples thereof particularly include animals of the family Felidae such as cats (*Felis silvestris catus*), lions (*Panthera leo*), and tigers (*Panthera tigris*), and animals of the family Canidae such as dogs (*Canis lupus familiaris*). The non-human animal is particularly preferably a cat, a dog, or a rat (*Rattus norvegicus*). The fEPO has high sequence identity to a dog-derived erythropoietin. Hence, the method according to one or more embodiments of the present invention is particularly effective for animals of the family Canidae including dogs, as in animals of the family Felidae and rats.

<Method>

The method according to one or more embodiments of the present invention is a method for inhibiting renal hypofunction in a non-human animal and relates to a method comprising a step of administering fEPO to the non-human animal.

In this context, the phrase "inhibiting renal hypofunction" refers to inhibiting decrease in function of the kidney, particularly, decrease in function of the kidney caused by chronic kidney disease (CKD). In one or more embodiments of the present invention, examples of the renal function whose decrease should be inhibited include renal functions such as tubular reabsorption, excretion of waste products (excretion of uremic toxin), glomerular filtration, adjustment of water balance in body fluids, adjustment of electrolyte (e.g., sodium, chlorine, potassium, and calcium) balance in body fluids, adjustment of acid-base balance in body fluids (pH adjustment), and hormone secretion. One or more embodiments of the present invention are particularly effective for inhibiting renal hypofunction that causes one or more changes selected from the group consisting of polydipsia/polyuria, elevation in creatinine concentration in blood, and elevation in blood urea nitrogen concentration. The present inventors have found that, surprisingly, the administration of fEPO inhibits such renal hypofunction, i.e., protects renal functions, in non-human animals. This effect can be called "renal protective" effect. Particularly, the effect of protecting renal functions by the administration of fEPO is an effect different from that of promoting hematopoiesis by the administration of fEPO.

The dosing frequency of the fEPO in the method according to one or more embodiments of the present invention is not particularly limited, and the fEPO is preferably administered at a time interval of a period of 7 days or longer, more preferably a period of 7 days or longer and 30 days or shorter. The period is specifically period defined by a preferred combination of the lower limit value which is 8 days or longer, 9 days or longer, 10 days or longer, 11 days or longer, 12 days or longer, 13 days or longer, 14 days or longer, 15 days or longer, 16 days or longer, 17 days or longer, 18 days or longer, 19 days or longer, 20 days or longer, 21 days or longer, 22 days or longer, 23 days or longer, 24 days or longer, 25 days or longer, 26 days or longer, 27 days or longer, 28 days or longer or 29 days or longer, and the upper limit value which is 29 days or shorter, 28 days or shorter, 27 days or shorter, 26 days or shorter, 25 days or shorter, 24 days or shorter, 23 days or shorter, 22 days or shorter, 21 days or shorter, 20 days or shorter, 19 days or shorter, 18 days or shorter, 17 days or shorter, 16 days or shorter, 15 days or shorter, 14 days or shorter, 13 days or shorter, 12 days or shorter, 11 days or shorter, 10 days or shorter, 9 days or shorter or 8 days or shorter. The treatment of renal anemia using fEPO requires continuously keeping the in vivo concentration of the fEPO high, and therefore, it may be necessary to administer the fEPO at a frequency as high as two or three times a week. For the purpose of inhibiting renal hypofunction, administration at the time interval of a relatively long period as described above suffices. Furthermore, such administration at the time interval of a relatively long period is preferred because pain of animals and burden on owners of the animals ascribable to outpatient treatment are minimized. The administration of the fEPO at a time interval of the period means that the procedure of administering the fEPO to the subject animal is performed on the basis of the period. The administration performed within each period described above is defined as "one-time" administration. In this context, the "one-time" administration may be administration based on a single administration operation or may be administration based on a plurality of administration operations performed for a given range of time, preferably 36 hours or shorter, more preferably 24 hours or shorter, more preferably 12 hours or shorter, more preferably 6 hours or shorter. The "one-time" administration is administration based on a single administration operation or administration based on a plurality of (preferably 2 or 3) administration operations performed for a time of 24 hours or shorter, more preferably 12 hours or shorter, more preferably 6 hours or shorter, particularly preferably administration based on a single administration operation, for reducing burden on the subject animal or its owner. The administration of the fEPO, for example, on the same day every week is administration at a 7-day time interval (or at a frequency of once 7 days). The administration of the fEPO on the same day every other week is administration at a 14-day time interval (or at a frequency of once 14 days). The fEPO may be administered by a plurality of administration operations for the day of administration. The one-time administration of the fEPO by a single or a plurality of administration operations that complete, for example, from Monday through Tuesday every week is also administration at a 7-day time interval (or at a frequency of once 7 days). The one-time administration of the fEPO by a single or a plurality of administration operations that complete from Monday through Tuesday every other week is also administration at a 14-day time interval (or at a frequency of once 14 days). The same holds true for other cases. Since renal hypofunction generally progresses gradually over a long period, it is preferred to perform continuously administer the fEPO at the time interval described above.

The dose of the fEPO per the period (i.e., the dose of the fEPO in the one-time administration) is not particularly limited and can be appropriately set according to the length of the dose interval or the required degree of inhibition of renal hypofunction. Every dose of the fEPO according to one or more embodiments of the present invention refers to a dose based on weight calculated in terms of the mature fEPO polypeptide that consists of the amino acid sequence represented by SEQ ID NO: 3 and does not undergo chemical modification with the water-soluble long-chain molecule or the like. The fEPO to be administered can be in various forms such as fEPO chemically modified with the water-soluble long-chain molecule or the like, as already mentioned. The dose of the fEPO in any form can be indicated by a dose based on weight calculated in terms of the polypeptide consisting of the amino acid sequence represented by SEQ ID NO: 3. The dose of the fEPO per the period is preferably 3 µg/kg body weight or larger, preferably 5 g/kg body weight or larger, preferably 7 g/kg body weight or larger, preferably 9 g/kg body weight or larger, preferably 10 g/kg body weight or larger, preferably 15 g/kg body weight or larger, preferably 20 g/kg body weight or larger, or preferably 25 g/kg body weight or larger, and preferably 400 g/kg body weight or smaller, preferably 350 g/kg body weight or smaller, preferably 300 g/kg body weight or smaller, preferably 250 g/kg body weight or smaller, preferably 200 g/kg body weight or smaller, preferably 150 g/kg body weight or smaller, or preferably 100 g/kg body weight or smaller. Provided that the dose of the fEPO falls within this range, the renal hypofunction inhibitory effect of interest can be achieved, and furthermore, continuously repeated administration is considered less likely to cause adverse reactions.

The amount of the fEPO described above can be determined by using an aqueous fEPO solution prepared from the fEPO to be quantified as a sample, measuring absorbance at wavelengths of 280 nm and 320 nm using a quartz cell having an optical path length of L cm and a spectrophotometer, and determining the fEPO concentration of the aqueous solution according to the following expression, followed by calculation on the basis of the concentration.

fEPO concentration (mg/mL)=(Abs280−Abs320)× 0.959/L    Expression:

The coefficient "0.959" of the expression is calculated on the basis of the molar absorption coefficient $1.90 \times 10^4$ ($L \cdot mol^{-1} \cdot cm^{-1}$) of the fEPO as to the difference in absorbance (Abs280−Abs320), determined by a test in consideration of the amino acid sequence (SEQ NO: 3) of the mature fEPO. Thus, the amount of the fEPO calculated in terms of the polypeptide consisting of the amino acid sequence represented by SEQ ID NO: 3 can be accurately evaluated according to the measurement method and the expression described above.

Meanwhile, existing methods for quantifying fEPO include cell growth assay using an EPO-dependent cell line BaF/EPOR (JP Patent Publication (Kokai) No. 10-94393 A (1998)), immunoassay using an anti-human EPO antibody (ELISA, etc.), and the like. Among these methods, the cell growth assay using BaF/EPOR is an assay system using cells having a receptor having high affinity for human EPO on the surface and is not suitable for quantifying fEPO. Likewise, the immunoassay using an anti-human EPO antibody employs the antibody nonspecific for fEPO and is therefore not suitable for the quantification of fEPO. The conventional quantification of fEPO involves using any of these methods, preparing a calibration curve with a known amount of fEPO as a sample, and then measuring the amount of fEPO in a sample to be analyzed. Therefore, the accurate quantification of fEPO is not easy for such an approach. Thus, it is not rational to merely compare the value of the amount of fEPO determined by such a conventional method with the value of the accurate amount of fEPO determined according to the expression described above by measuring the absorbance of the aqueous fEPO solution at wavelengths of 280 nm and 320 nm.

In the method according to one or more embodiments of the present invention, the administration route of the fEPO to the non-human animal is not particularly limited and may be oral administration or parenteral administration. Examples of the parenteral administration include intravenous administration, subcutaneous administration, intracutaneous administration, intramuscular administration, transdermal administration, and transmucosal administration (transnasal administration, administration by eye drops, etc.). The administration route is particularly preferably subcutaneous administration or intracutaneous administration.

In one or more embodiments of the method of the present invention, the non-human animal serving as a recipient is a non-human animal in need of inhibition of renal hypofunction at least at the start of the administration step. The non-human animal in need of inhibition of renal hypofunction is typically a non-human animal having or suspected of having chronic kidney disease. Whether a non-human animal has or is suspected of having chronic kidney disease is determined by the professional judgment of a veterinarian. The non-human animal can be confirmed to have or be suspected of having chronic kidney disease when the non-human animal satisfies or is suspected of having at least one of (1) kidney damage (demonstrated from tissues, blood, urinalysis or diagnostic imaging) that has been present for at least 3 months, and (2) reduction in glomerular filtration rate (GFR) (50% or more reduction in GFR from the normal level) that has been present for at least 3 months, according to the definition of Non Patent Literature 2. More conveniently, this may also be confirmed according to the chronic kidney disease staging system defined by the International Renal Interest Society (see Non Patent Literatures 1, 3 and 4). The non-human animal can be regarded as having chronic kidney disease when the non-human animal can be classified into stage I or higher according to the staging system. The non-human animal can be regarded as being suspected of having chronic kidney disease when the non-human animal can be classified into "at risk". Also, the non-human animal can be regarded as being suspected of having chronic kidney disease when the non-human animal manifests a symptom of chronic kidney disease but has not yet received definitive diagnosis by a veterinarian.

In one or more embodiments of the method of the present invention, more preferably, the non-human animal serving as a recipient is free from anemia, particularly, renal anemia, at least at the start of the administration step. Whether or not a non-human animal has anemia is determined by the professional judgment of a veterinarian. The non-human animal can be confirmed to have anemia by using its hematocrit level that falls below the lower limit value in the range of normal levels as an index, and can be confirmed to be free from anemia when the hematocrit level is equal to or higher than the lower limit value. The range of normal levels of the hematocrit level and the lower limit value thereof can be appropriately set according to the animal species and are not particularly limited. The non-human animal can be confirmed to have anemia, for example, when the hematocrit level in an adult is 24% or lower for cats, 36% or lower for dots, and 40% or lower for rats, and can be confirmed to be free from anemia when the hematocrit level is larger than 24% for cats, larger than 36% for dogs, and larger than 40% for rats. Renal anemia is anemia that is caused by the reduced production of endogenous erythropoietin in association with the progression of kidney disease, which is combined with reduced nutrition, iron deficiency, bleeding tendency, shortened life span of red blood cells, etc. The renal anemia is usually a symptom that appears at the late stage of chronic kidney disease. Renal functions still remain sufficiently at a stage before onset of anemia. Therefore, the administration of fEPO started from this stage is particularly highly effective for inhibiting renal hypofunction and can effectively delay the progression of chronic kidney disease. According to the staging system, a non-human animal having or suspected of having chronic kidney disease classified into stage I or stage II is free from renal anemia.

In one or more embodiment of the method of the present invention, it is preferred to start the fEPO administration step from the stage where the non-human animal serving as a recipient has or is suspected of having chronic kidney disease classified into stage I or stage II based on the staging system at least at the start of the administration step.

In the chronic kidney disease staging system, the term "at risk" means to suggest as to the subject non-human animal from its history that the risk of having chronic kidney disease in the future is increased due to some factors. Examples of the factors can include one or more factors selected from exposure to a nephrotoxic medicament, bleeding, regional spreading of an infectious disease, and aging.

In the chronic kidney disease staging system, stage I is a stage that is nonazotemic and has other kidney abnormalities. At stage I, the creatinine concentration in blood is lower than 1.6 for cats and lower than 1.4 for dogs. Examples of the other kidney abnormalities can include one or more abnormalities selected from (A) inadequate urinary concentrating ability without identifiable non-renal cause, (B) abnormal renal palpation or renal imaging findings, (C) proteinuria of renal origin, (D) abnormal renal biopsy results, and (E) increasing blood creatinine concentrations in samples collected serially.

In the chronic kidney disease staging system, stage II refers to mild renal azotemia. The creatinine concentration in blood serving as a reference for stage II is 1.6 to 2.7 mg/dL for cats and 1.4 to 1.9 mg/dL for dogs.

In one or more embodiments of the method of the present invention, it is also preferred for non-human animals other than cats and dogs to start the fEPO administration step from the stage having or suspected of having early chronic kidney disease.

In this context, whether or not a non-human animal has early chronic kidney disease can be determined on the basis of the presence or absence of kidney abnormalities and a creatinine concentration in blood. For example, when a non-human animal is found to have kidney abnormalities and has a creatinine concentration in blood that falls within the range of normal levels compared with an animal of the same species thereas, the non-human animal is regarded as being at the stage having early chronic kidney disease. In this context, examples of the kidney abnormalities can include one or more abnormalities selected from (A) to (E) listed above as to IRIS stage I. As for rats, a creatinine concentration in blood of 0.5 mg/dL or lower is regarded as falling within the range of normal levels.

Whether the non-human animal serving as a recipient has not yet led to the late stage of chronic kidney disease can be determined by using a creatinine concentration in blood as an index. When the non-human animal has a creatinine concentration in blood of preferably 2.7 mg/dL or lower at least at the start of the administration step, it can be confirmed that the non-human animal has not yet led to the late stage of chronic kidney disease. The administration of fEPO started from this stage is particularly highly effective for inhibiting renal hypofunction. More specifically, when a cat as the non-human animal has a creatinine concentration in blood of preferably 2.7 mg/dL or lower, more preferably lower than 1.6 mg/dL, at least at the start of the administration step, when a dog as the non-human animal has a creatinine concentration in blood of preferably 1.9 mg/dL or lower, more preferably lower than 1.4 mg/dL, at least at the start of the administration step, or when a rat as the non-human animal has a creatinine concentration in blood of preferably 0.5 mg/dL or lower, more preferably lower than 0.4 mg/dL, at least at the start of the administration step, it can be confirmed that the non-human animal has not yet led to the late stage of chronic kidney disease.

The creatinine concentration in blood can be measured by use of an enzyme method and can be measured using a commercially available kit for creatinine concentration measurement.

The "creatinine concentration in blood" is called "plasma creatinine concentration" when measured with plasma as a sample, and called "serum creatinine concentration" when measured with serum as a sample. In both the cases, the creatinine concentration is the same value. In Examples described below, the creatinine concentration in blood was measured with plasma as a sample.

When the non-human animal has or is suspected of having chronic kidney disease but is free from anemia and, for example, when this non-human animal is found to have kidney abnormalities listed above and has a hematocrit level that falls within the range of normal levels compared with an animal of the same species thereas, the non-human animal can be confirmed to have early chronic kidney disease. The exemplary range of hematocrit levels that can indicate the absence of anemia is as already mentioned.

<Combined Use with Additional Method>

The method for inhibiting renal hypofunction according to one or more embodiments of the present invention may be performed in combination with an additional step. Examples of the additional step can include at least one step selected from the group consisting of taking iron supplementation, administering intravenous fluids, performing dialysis, performing diet therapy, administering an antihypertensive agent, administering an adsorbent, and administering vitamin. The additional step is preferably a step useful as a method for inhibiting renal hypofunction. At least one step selected from administering intravenous fluids, administering an antihypertensive agent, and administering a diuretic, which are not used for the direct purpose of an effect of promoting hematopoiesis, is particularly preferably used in combination with the fEPO administration method according to one or more embodiments of the present invention for inhibiting renal hypofunction.

The step of taking iron supplementation is effective for inhibiting renal anemia. The iron supplementation can be performed by orally or parenterally administering an iron preparation. For example, iron sulfate, sodium ferrous citrate, ferrous orotate, ferrous fumarate, ferrotrenine, ferric pyrophosphate, chondroitin sulfate-iron, saccharated ferric oxide, ferric gluconate, or cideferron (all are generic names) can be used as the iron preparation. Among them, iron sulfate, sodium ferrous citrate, ferrous orotate, ferrous fumarate, ferrotrenine and ferric pyrophosphate are suitable for oral administration, while chondroitin sulfate-iron, saccharated ferric oxide, ferric gluconate and cideferron are suitable for parenteral administration (specifically, intravenous administration).

The step of administering intravenous fluids is effective as a method for inhibiting renal hypofunction, particularly, decrease in one or more renal functions selected from adjustment of water balance in body fluids, adjustment of electrolyte balance in body fluids and adjustment of acid-base balance in body fluids. In the method according to one or more embodiments of the present invention for inhibiting renal hypofunction, combined use of the step of administering fEPO with the step of administering intravenous fluids can reduce the amount of the infusion administered as intravenous fluids and the dosing frequency of the intravenous fluids and can reduce burden on the subject non-human animal and its owner.

For example, an infusion described in a general literature such as "Small Animal Clinical Pharmacotherapeutics, Hirashi Ozaki, Fumitoshi Asai, Hajime Tsujimoto, Ohmsha, Ltd., Tokyo, Japan (2010)" or "List of Intravenous Solution Composition, The Intravenous Solutions Society (Composition Table Search|The Intravenous Solutions Society)" can be used. Hereinafter, specific examples thereof will be described.

The infusion can be classified into electrolyte infusions, water infusions, nutrient infusions, plasma expanders, and the like, all of which can be preferably used.

Examples of the electrolyte infusions include isotonic extracellular fluid-like solutions, hypotonic composite electrolytes, and hypertonic (single) electrolyte infusions. Examples of the isotonic extracellular fluid-like solutions can include saline, Ringer's solutions, lactated Ringer's solutions (Hartmann's solutions), acetated Ringer's solutions and bicarbonated Ringer's solutions. Examples of the hypotonic composite electrolytes can include starting solutions (No. 1 solutions), intracellular repair solutions (No. 2 solutions and rehydration solutions), maintenance solutions (No, 3 solutions), postoperative recovery solutions (No. 4 solutions), and other solutions such as Physio 70 injections. Examples of the hypertonic (single) electrolyte infusions can include NaCl infusions, K infusions, Ca infusions, Mg infusions, P infusions, alkalizing agents (sodium bicarbonate and sodium lactate) and acidifying agents (ammonium chloride).

Examples of the water infusions can include 5% glucose solutions.

Examples of the nutrient infusions include calorie producing agents and non-heat producing agents. Examples of the calorie producing agents can include carbohydrate infusions (glucose solutions, xylitol solutions, sorbitol solutions, and maltose solutions), lipid infusions (soybean oil), amino acid infusions (high-concentration amino acid solutions, amino acid solutions for renal failure, amino acid solutions for hepatic failure, and amino acid solutions for children), and high-calorie infusions (mixed infusions of some or all of a sugar, an electrolyte, an amino acid, vitamin, lipid, and a trace element). Examples of the non-heat producing agents can include vitamin preparations and trace elements (ferric chloride/zinc sulfate hydrate and manganese chloride/zinc sulfate hydrate).

Examples of the plasma expanders include colloid solutions and osmotic pressure infusions. Examples of the colloid solutions can include colloid solutions containing low-molecular-weight dextran, hydroxyethyl starch or gelatin. Examples of the osmotic pressure infusions can include osmotic pressure infusions containing mannitol or glycerol.

The step of performing dialysis is effective as a method for inhibiting renal hypofunction, particularly, decrease in function of excreting waste products. In the method according to one or more embodiments of the present invention for inhibiting renal hypofunction, combined use of the step of administering IPO with the step of performing dialysis can reduce the frequency of the dialysis and can reduce burden on the subject non-human animal and its owner.

The step of performing diet therapy is effective as a method for inhibiting renal hypofunction. In the method according to one or more embodiments of the present invention for inhibiting renal hypofunction, combined use of the step of administering fEPO with the step of performing diet therapy can elevate the frequency and amount of ingestion of ordinary food and can reduce burden on the subject non-human animal and its owner.

In the diet therapy for inhibiting renal hypofunction, the non-human animal can generally be allowed to consume a diet with a limited intake of one or more components selected from protein, salt (electrolyte), potassium and phosphorus. A protein-restricted diet is generally supplemented with fat and oil in order to prevent decrease in caloric intake ascribable to the reduced amount of protein.

In the diet therapy, the non-human animal may be allowed to consume a diet supplemented with a health food material, a dietary supplement material, or the like, generally used for humans. The diet for inhibiting renal hypofunction may be supplemented with one or more of these materials, or an ordinary diet may be supplemented with one or more of these materials.

Examples of the health food material include, but are not particularly limited to, Chinese herbal medicines (e.g., Ireito, Unkeito, Unseiin, Ogikenchuto, Orengedokuto, Orento, Kakkonto, Kamikihito, Kamishoyosan, Kanbakutaisoto, Kikyoto, Kihito, Kumibinroto, Keigairengyto, Keishikashakuyakudaioto, Keishikashakuyakuto, Keishikaryukotsuboreito, Keishito, Keishininijinto, Keishibukuryogan, Keihito, Kososan, Gokoto, Goshakusan, Goshajinkigan, Gorinsan, Saikanto, Saikokagukotsuboreito, Saikokeishikankyoto, Saikokeishito, Saikoseikanto, Saibokuto, Saireito, Sansoninto, Jiinkokato, Shigyakusan, Shikunshito, Shimotsuto, Shakanzoto, Shakuyakukanzoto, Juzentaihoto, Jumihaidokuto, Shokenchuto, Shosaikoto, Shoseiryuto, Shofusan, Shiniseihaito, Shimpito, Shimbuto, Seijobofuto, Seishoekkito, Seishinrenshiin, Seihaito, Sokeikakketsuto, Daiokanzoto, Daiobotanpito, Daikenchuto, Daisaikoto, Daisaikotokyodaio, Daijokito, Daibofuto, Jidabokuippo, Choijokito, Chotosan, Choyoto, Choreito, Choreitogoshimotsuto, Tsudosan, Tokakujokito, Tokiinshi, Tokikenchuto, Tokishakuyakusan, Tokito, Nichinto, Nyoshinsan, Ninjinto, Ninjinyoeito, Hainosankyuto, Bakumondoto, Hachimijiogan, Hangekobokuto, Hangeshoshinto, Byakkokaninjinto, Bukuryoin, Bukuryoingohangekohokuto, Heiisan, Boiohito, Bofutsushosan, Hochuekkito, Maoto, Maobushisaishinto, Makyokansekito, mashiningan, Mokuboito, Yokukansan, Yokukansankachinpihange, Rikkunshito, Rikkosan, Ryutanshakanto, Ryokankyomishingeninto, and Rokumigan), tea leaves (e.g., green tea, brown rice tea, powdered green tea, green tea of middle grade, roasted green tea, roasted green tea, jasmine tea, oolong tea, red tea, black tea, flowering tea, blue tea, and white tea), herbs (e.g., Italian parsley, elecampane, olive, oregano, cardoon, chamomile, curry plant, catnip, caraway, Christmas rose, crimson clover, corn flour, common mallow, salad burnet, santolina, cinnamon, jasmine, stevia, sage, common linden, scented geranium, St. John's wort, soapwort, Solomon's seal, thyme, tansy, chervil, chive, nasturtium, jujube, basil, honey suckle, hyssop, flax, fennel, foxglove, black hollyhock, French marigold, betony, heliotrope, bergamot, hemp agrimony, common rue, pot marigold, borage, white horehound, myrtle, common mullein, marjoram, mint, yarrow, lavender, lady's bedstraw, lemongrass, lemon verbena, lemon balm, rose, rosemary, rocket, wild strawberry, wild pansy, and myosotis), propolis, ginkgo leaves, green juice and their extracts.

Examples of the dietary supplement materials include, but are not particularly limited to, amino acids, metal ions, proteins, saccharides, fatty acids (particularly, polyvalent unsaturated fatty acids derived from fat and oil such as fish oil, for example, ω3 unsaturated fatty acids, ω6 unsaturated fatty acids, and ω9 unsaturated fatty acids), yeast extracts, vegetable extracts, fish meat extracts, fruits, fruit extracts, N-acetylglucosamine, S-adenosylmethionine, tetrahydrobiopterin, and coenzyme Q.

The step of administering an antihypertensive agent is effective as a method for inhibiting renal hypofunction. In the method according to one or more embodiments of the present invention for inhibiting renal hypofunction, combined use of the step of administering fEPO with the step of administering an antihypertensive agent can reduce the dosing frequency and dose of the antihypertensive agent and can reduce burden on the subject non-human animal and its owner.

The antihypertensive agent can be classified into β blockers, α,β blockers, α blockers, sympathetic blocking agents, calcium antagonists, ACE inhibitors, AII receptor antagonists, direct renin inhibitors, vascular smooth muscle agonists, and the like, any of which can be used in one or more embodiments of the present invention. Examples of the β blockers can include propranolol, nipradilol, tilisolol, nadolol, carteolol, pindolol, atenolol, metoprolol, betaxolol, bisoprolol, acebutolol, and celiprolol. Examples of the α,β blockers can include labetalol, amosulalol, carvedilol, arotinolol, and bevantolol. Examples of the α blockers can include prazosin, doxazosin, bunazosin, terazosin, and urapidil. Examples of the sympathetic blocking agents can include clonidine, α methyldopa, guanabenz, guanfacine, reserpine, and trimetaphan. Examples of the calcium antagonists can include diltiazem, nifedipine, nicardipine, nisoldipine, nitrendipine, nilvadipine, amlodipine, benidipine, efonidipine, azelnidipine, manidipine, cilnidipine, aranidipine, felodipine, and barnidipine. Examples of the ACE inhibitors can include captopril, enalapril, lisinopril, alacepril, imidapril, tetrocapril, perindopril, delapril, benazepril, cilazapril, quinapril, and trandolapril. Examples of the AII receptor antagonists can include losartan, candesartan cilexetil, valsartan, telmisartan, irbesartan, olmesartan, and azilsartan. Examples of the direct renin inhibitors can include aliskiren. Examples of the vascular smooth muscle agonists can include hydralazine and budralazine.

The step of administering an adsorbent is effective as a method for inhibiting renal hypofunction, particularly, decrease in function of excreting waste products. In the method according to one or more embodiments of the present invention for inhibiting renal hypofunction, combined use of the step of administering fEPO with the step of administering an adsorbent can reduce the dosing frequency and dose of the adsorbent and can reduce burden on the subject non-human animal and its owner.

Examples of the adsorbent that can be used in one or more embodiments of the present invention can include, but are not particularly limited to, active carbon (medicinal carbon), aluminum silicate, magnesium silicate, precipitated calcium carbonate, sevelamer hydrochloride, bixalomer, ferric citrate hydrate, lanthanum carbonate, calcium polystyrenesulfonate, sodium polystyrenesulfonate, colestimide, and niceritrol.

The step of administering vitamin is effective as a method for inhibiting renal hypofunction. In the method according to one or more embodiments of the present invention for inhibiting renal hypofunction, combined use of the step of administering fEPO with the step of administering vitamin can reduce the dosing frequency and dose of the vitamin and can reduce burden on the subject non-human animal and its owner.

Examples of the vitamin that can be used in one or more embodiments of the present invention include, but are not particularly limited to, one or more vitamins selected from the group consisting of vitamin A, vitamin vitamin C, vitamin vitamin E and vitamin K, and their derivatives and can particularly include vitamin D.

The step of administering a diuretic is effective as a method for inhibiting renal hypofunction. In the method according to one or more embodiments of the present invention for inhibiting renal hypofunction, combined use of the step of administering fEPO with the step of administering a diuretic can reduce the dosing frequency and dose of the diuretic and can reduce burden on the subject non-human animal and its owner.

Examples of the diuretic that can be used in one or more embodiments of the present invention can include, but are not particularly limited to, trichloromethiazide, hydrochlorothiazide, benzylhydrochlorothiazide, indapamide, mefruside, tripamide, meticrane, furosemide, ethacrynic acid, torasemide, spironolactone, triamterene, and eplerenone.

The specific examples described above about the antihypertensive, the adsorbent, and the diuretic are disclosed in "NEW Pharmacology (revised 4th edition), Chikako Tanaka and Ryuichi Kato ed., Nankodo Co., Ltd., Tokyo, Japan (2002)", "Guidelines for the Management of Hypertension 2014, issued by The Japanese Society of Hypertension", etc.

<Medicament for Non-Human Animal Rise>

One or more embodiments of the present invention also relate to a medicament for non-human animal use for inhibiting renal hypofunction in a non-human animal, the medicament comprising fEPO.

One or more embodiments of the present invention also relate to use of fEPO for manufacturing the medicament.

The medicament can comprise at least fEPO and may further comprise a pharmaceutically acceptable additional component. The medicament is preferably a medicament composition comprising fEPO and a pharmaceutically acceptable additional component.

The form of the medicament according to one or more embodiments of the present invention is appropriately selected according to an administration route. Examples thereof include: forms of formulations for parenteral administration such as injections, drops, injectable fillers, solutions for external use, patches, liniments (creams, ointments, etc.), inhalants, sprays, suppositories, rectal capsules, subcutaneous implant-type sustained-release formulations, micelle formulations, gelling formulations, liposome formulations, and pessaries for intravaginal administration; and forms of formulations for oral administration. Examples of the application of the injections and the drops include intravenous application, subcutaneous application, intracutaneous application, intramuscular application, intraorgan application, intranasal application, eye drops, application into the brain, intraperitoneal application, and application to lesions. The injections may be in the form of a prefilled syringe formulation. Examples of the application of the injectable fillers include intrarectal application and intravaginal application. Examples of various formulations for oral administration include: solid formulations such as tablets, pills, capsules, powders, fine granules, and granules; and liquid formulations such as extracts, elixirs, syrups, tinctures, and lemonades. Among the medicaments in these forms, a formulation containing fEPO dissolved in a liquid is hereinafter referred to as a "solution formulation". Examples of the solution formulation include injections, drops, and injectable fillers. When the medicament is in the form of a solution formulation, a fEPO-containing solution formulation having the same osmotic pressure and pH as those of the body fluid of the subject non-human animal is preferred because the fEPO-containing solution formulation is less likely to cause pain when subcutaneously administered to the animal. In the case of manufacturing, for example, a solution formulation suitable for administration to a non-human animal having a body fluid with an osmotic pressure of approximately 280 mOs/kg $H_2O$ and pH of approximately 7.4, the solution formulation has an osmotic pressure of preferably 200 mOsm/kg $H_2O$ or higher and 400 mOsm/kg $H_2O$ or lower, more preferably 250 mOsm/kg $H_2O$ or higher and 300 mOsm/kg $H_2O$ or lower, and pH of preferably 7.0 or higher and 8.0 or lower, more preferably 7.3 or higher and 7.7 or lower. When the osmotic pressure of the body fluid of the non-human animal is defined as X mOsm/kg $H_2O$, the osmotic pressure of the solution formulation may be preferably (X±100) mOsm/kg $H_2O$, more preferably (X±50) mOsm/kg $H_2O$. When the pH of the body fluid of the non-human animal is defined as Y, the pH of the solution formulation may be preferably (Y±0.5), more preferably (Y±0.1). In this context, the osmotic pressure and the pH refer to values measured at 20 to 25° C.

The pharmaceutically acceptable additional component that may be contained in the medicament according to one or more embodiments of the present invention is not particularly limited and can be appropriately selected according to the form of interest. Examples of the pharmaceutically acceptable additional component include solvents (water, etc.), excipients, disintegrants, binders, stabilizers, adjusters, osmotic pressure adjusters, surfactants, lubricants, coating agents, colorants, aggregation inhibitors, absorption promoters, solubilizing agents, flavors, sweeteners, antiseptics, preservatives, and antioxidants.

One or more embodiments of the medicament of the present invention can be used in the method according to one or more embodiments of the present invention for inhibiting renal hypofunction in a non-human animal as described above, and specific forms of usage thereof are as already mentioned. The medicament according to one or more embodiments of the present invention can be used in combination with the additional method described above.

The medicament according to one or more embodiments of the present invention preferably comprises fEPO such that the fEPO is administered at the preferred dose per the period. Specifically, the medicament according to one or more embodiments of the present invention preferably comprises fEPO at the preferred dose (preferably 3 μg/kg body weight or larger and 400 μg/kg body weight or smaller, or the more preferred dose described above) per amount to be administered at an interval of the period (preferably a period of 7 days or longer and 30 days or shorter, or the more preferred period described above). The medicament in the amount may be a medicament in an amount to be administered by a single administration operation, or may be a medicament in an amount to be administered by a plurality of administration operations.

EXAMPLES

Hereinafter, one or more embodiments of the present invention will be described in detail with reference to Examples. However, the present invention is not limited by these Examples. When a trade name was described, the operation was performed in accordance with direction of the instruction manual attached thereto unless otherwise specified.

In tests described below, every dose and amount of PEGylated feline erythropoietin (PEGylated fEPO) are a dose based on weight calculated in terms of the mature fEPO polypeptide consisting of the amino acid sequence of SEQ ID NO: 3 without chemical modification with the water-soluble long-chain molecule or with any other molecule.

In animal test described below, every "PEGylated fEPO" refers to a PEGylated form of mature fEPO (SEQ ID NO: 3).

<Preparation Example: Preparation of PEGylated fEPO>

According to the following procedures, cat-derived erythropoietin (fEPO)-containing egg whites were prepared from a transgenic chicken and PEGylated, and then, a formulation for administration was prepared.

(1. Preparation of Egg White Containing fEPO Using Transgenic Chicken)

The fEPO-containing egg whites were prepared by a modification of a method based on the method described in JP Patent Publication (Kokai) No. 2007-89578 A (2007). The key points of the process will be described below.

(1.1. Microinjection of Retrovirus Vector to Chicken Embryo and Artificial Hatching)

Retrovirus vectors for fEPO expression were injected to chicken embryos to prepare transgenic chickens expressing fEPO. The microinjection and the artificial hatching were performed under aseptic conditions.

The nucleotide sequence of DNA encoding fEPO (full-length preprotein) is shown in SEQ ID NO: 1.

A solution containing the retrovirus vectors for fEPO expression, prepared by the method of Example 5 of JP Patent Publication (Kokai) No. 2007-89578 A (2007) was used. The method for measuring a virus titer is as described in Example 3 of JP Patent Publication (Kokai) No. 2007-89578 A (2007).

The outside of the chicken fertilized eggs was disinfected with an antiseptic solution (manufactured by Showa Frankie K. K.) and ethanol. An incubator model P-008 (B) (manufactured by Showa Frankie K. K.) was set to an environment of 38° C. and 50 to 60% humidity. The time when the incubator was switched on was defined as the start time of incubation (0 hours). Subsequently, the eggs were incubated while turned 90° every 15 minutes.

After a lapse of approximately 55 hours from the start of incubation, the eggs were taken out of the incubator, and a hole of approximately 1 mm was made at the blunt end. Subsequently, a hole of approximately 7 to 10 mm in diameter was made in a portion slightly above the center at the side of the eggs. Approximately 2 μl of the virus solution prepared by the procedures described in Example 5 of JP Patent Publication (Kokai) No. 2007-89578 A (2007) was injected to FemtoTips II (manufactured by Eppendorf AG) under a stereoscopic microscope system SZX12 (manufactured by Olympus Corp.) and injected to the hearts of the chicken embryos through the hole using FemtoJet (manufactured by Eppendorf AG).

After the injection of the virus solution, the holes were closed with Scotch Tape BK-15 (manufactured by 3M Company). The eggs were brought back to the incubator, and the incubation was continued. The turning of the eggs in the incubator was changed to the turning of the eggs 30° every 30 minutes. After 1 week from the start of incubation, oxygen was supplied at 60 cc/min to the incubator where the eggs were then incubated. On the 19th day from the start of incubation, the turning of the eggs was stopped, and the eggs were allowed to hatch spontaneously. The chicks that emerged by spontaneous hatching were raised and allowed to grow to obtain female adults of transgenic chickens. SX Safety and Neo-Safety 17 for young chicks (available from Toyohashi Feed Mills Co., Ltd.) were used as feed. The expression of fEPO in the eggs of the transgenic chickens was confirmed by cell growth assay using BaF/EPOR mentioned later. The fEPO activity in the egg whites was confirmed to be $1.4 \times 10^4$ U/mL.

The eggs of chicken individuals confirmed to have fEPO activity in the egg whites were recovered, broken using a diamond cutter-type egg breaker (manufactured by Mitaka Electric Co., Ltd.), and separated into egg whites and egg yolks using an egg white separation slit (manufactured by Mitaka Electric Co., Ltd.). Only the egg whites were recovered. The recovered egg whites were sheared through an egg white strainer having an aperture of 1 mm (manufactured by Sankyo Research & Development). 10 to 20 L of the sheared egg whites were recovered into a 20 L tank and mixed by stirring using a stirrer. The egg whites were cryopreserved using a freezer of −80° C. (CLN-50CD1 manufactured by Nihon Freezer Co., Ltd.) until use in purification.

(1.2. fEPO Activity Measurement)

The activity of fEPO in the egg whites was evaluated by cell growth assay using an EPO-dependent cell line BaF/EPOR (JP Patent Publication (Kokai) No. 10-94393 A (1998)). The cell growth assay involved drawing a calibration curve for growth using Epozine (manufactured by Chugai Pharmaceutical Co., Ltd.) as standard erythropoietin, and measuring the erythropoietin activity of a test sample on the basis of the calibration curve. RPMI1640 liquid medium (manufactured by Nissui Pharmaceutical Co., Ltd.) containing 5% fetal bovine serum (FBS) and 50 units/ml of penicillin and streptomycin was used as a medium for BaF/EPOR cells. Epozine was added at a final concentration of 1 U/ml for the ordinary culture of BaF/EPOR cells. The cell growth assay employed cells at the logarithmic growth phase.

In order to conduct the cell growth assay using BaF/EPOR cells, first, Epozine in the medium was removed. The cultured BaF/EPOR cells were centrifuged at 1000 rpm for minutes. The supernatant was removed, and the precipitates were suspended by the addition of 10 ml of an Epozine-free medium. The same operation thereas was performed three times to remove Epozine in the medium. The cells were counted and diluted to a concentration of 55555 cells/ml with an Epozine-free medium. 90 μl of the dilution was inoculated to each well of a 96-well microliter plate. 10 μl of Epozine diluted to 25, 16, 10, 6.4, 4.0, 2.5, 1.6, or 1.0 U/ml with a medium was added to each well of this plate for homogeneous suspension (final concentration of erythropoietin: 2.5, 1.6, 1.0, 0.64, 0.4, 0.25, 0.16, or 0.1 U/ml, respectively).

The sample used in the assay was serially diluted approximately 2- to 4-fold with a medium so as to fall within the measurement range of the calibration curve. 10 μl of the dilution was added to the cells inoculated in each well for homogeneous suspension. Three identical samples were measured as each of the standard sample and the test sample. The cells were cultured for 2 days, and 10 μl of Cell Counting Kit-8 (manufactured by Dojindo Laboratories) solution was added to each well. After color reaction for 1 to 4 hours, the reaction was terminated by the addition of 10 μl of 0.1 mol/l hydrochloric acid, followed by the measurement of absorbance at 450 nm using a microplate reader. An approximate expression was determined by the logarithmic approximation of the results of measuring the standard sample. The activity of the test sample was calculated according to the determined approximate expression.

The egg white samples used in the activity measurement were prepared so as to be entirely homogeneous by ultrasound or a physical approach. The prepared sample was cryopreserved at −80° C. until activity measurement.

(2. Purification of fEPO)

From the fEPO-containing chicken egg white solution obtained in the preceding section 1, a purified fEPO fraction was obtained by approaches such as a plurality of column chromatography techniques and ultrafiltration in combination.

The purified fEPO fraction contained a 50 mM phosphate buffer solution (pH 8.35) as a buffer solution and had a fEPO concentration of 2.3 mg/mL and biological activity of $2.8 \times 10^5$ U/mg (according to the method described in the section 1.2. fEPO activity measurement).

(3. PEGylation of fEPO)

The following PEGylating agent was added to the purified fEPO fraction obtained in the preceding section 2.

SUNBRIGHT ME-200HS (PEGylating agent of linear PEG having an average molecular weight of 20 K, manufactured by NOF Corp.)

The purified fEPO fraction and the PEGylating agent were mixed at a fEPO:PEGylating agent molar ratio of 1:5 and then reacted for 2 hours with mixing at 4° C. After the reaction for 2 hours, a 100 mM glycine solution was added as a reaction terminator in an amount of 1/10, and the reaction was terminated with stirring at 4° C. for 1 hour.

Subsequently, the PEGylation reaction solution was diluted with a 10-fold amount of a 50 mM acetic acid-sodium acetate buffer solution (pH 4.5) and filtered through a 0.2 μm filter. Then, a mono-PEGylated fEPO, a di- PEGylated fEPO, an oligo-PEGylated fEPO, unreacted PEG, and unreacted fEPO were separated and recovered by chromatography.

Eluted fractions corresponding to the peaks of the recovered mono-PEGylated fEPO and di-PEGylated fEPO were evenly stirred to prepare a "MCSP eluted fraction".

From the MCSP eluted fraction described above, a PEGylated fEPO bulk was prepared through steps such as ultrafiltration and virus removal.

(4. Formulation)

From the PEGylated fEPO bulk described above, a liquid composition was manufactured according to the composition of Table 1 below.

TABLE 1

| | | Final concentration (mg/mL) |
|---|---|---|
| Active ingredient | PEGylated fEPO | 0.11 |
| Additive | Glycine | 1 |
| | Sodium dihydrogen phosphate dihydrate | 3.12 |
| | Sodium chloride | 6.7 |
| | Tween 80 | 0.05 |
| pH | 7.5 ± 0.2 (adjusted with 1N NaOH) | |

PEGylated fEPO concentration: Absorbance at wavelengths of 280 nm and 320 nm was measured using a spectrophotometer and a quartz cell having an optical path length of 2 cm, and the PEGylated fEPO concentration was calculated according to the following expression and was consequently 0.11 mg/mL.

$$\text{PEGylated fEPO concentration} = (Abs280 - Abs320) - 0.959/2 \quad \text{Expression:}$$

Biological activity measurement: The biological activity was determined according to the method described in the preceding section "1.2. fEPO activity measurement". The formulation was diluted (2000-fold to 5000-fold) and added to the culture solution. After culture in an atmosphere of 37° C. and 5% $CO_2$ for 2 days, Cell Counting Kit 8 (Dojindo Laboratories) was added thereto, followed by the measurement of the cell count. A standard curve was prepared, and the activity was read out. The specific activity of the formulation was calculated and was consequently $1.8 \times 10^4$ U/mg.

<Test 1: Long-Term Administration of PEGylated fEPO to Chronic Kidney Disease Model Rat>

(Summary)

The PEGylated feline erythropoietin (hereinafter, referred to as PEGylated fEPO) prepared in the Preparation Example was evaluated for its pharmaceutical efficacy on chronic kidney disease using hypoplastic kidney (HPK) rats maintained at the Faculty of Veterinary Science, School of Veterinary Medicine, Laboratory of Veterinary Physiology, Nippon Veterinary and Life Science University. The PEGylated fEPO was administered for a long term at repeated doses of 36.6 μg/kg body weight every 14 days to a 10-week-old male HPK rat and a male normal rat until the rats reached 30 weeks old. Increased hematopoiesis over a long period was observed in the normal rats by the administration of 36.6 μg/kg body weight. A HPK rat given a vehicle saline exhibited an upward tendency of blood urea nitrogen (BUN) and creatinine (Cre), whereas the administration of the PEGylated fEPO reduced these levels. Also, polydipsia/polyuria remarkably progressed in HPK rat given saline, whereas the administration of the PEGylated fEPO prevented polydipsia/polyuria. These results suggested that the long-term administration of the PEGylated fEPO inhibits deterioration in renal functions.

(Object)

PEGylated fEPO can be administered a plurality of times to cats and is maintained for a long period in their bodies (see Tests 3, 4, and 5). Hence, the PEGylated fEPO is expected to inhibit the progression of renal failure or improve prognosis thereof by a fewer number of doses from the early stage. Accordingly, an object of this test is to perform the long-term continuous administration of PEGylated fEPO from the early stage of the disease to HPK rats and to confirm whether to exhibit a renal protective effect or an inhibitory effect on the progression of renal failure.

(Method)

HPK rats were produced as needed, and the administration of a test substance was started at the point in time when the obtained rat individuals reached the age of the experimental starting date (10 weeks old), followed by sampling.

The HPK rats have abnormalities in the kidney by nature, are free from anemia at the start of administration of PEGylated fEPO, and have a normal level of Cre concentration in blood. Thus, the HPK rats are regarded as having early chronic kidney disease corresponding to stage I based on the IRIS staging at least at the start of administration of PEGylated fEPO.

Test Substance:

PEGylated fEPO prepared in the Preparation Example

Dosing Solution Preparation:

The test substance prepared in the Preparation Example was refrigerated until immediately before use. The solution was left standing at room temperature immediately before administration, and the solution that reached approximately room temperature was subcutaneously administered using a 27 G injection needle.

Rearing Environment:

Each subject was allowed to freely consume CR-LPF (manufactured by Oriental Yeast Co., Ltd.) as feed and freely drink tap water from a water supply bottle (manufactured by Tokiwa Kagaku Kikai Co., Ltd.).

Administration:

The PEGylated fEPO was subcutaneously administered at a dose of 36.6 μg/kg body weight. Saline was administered at the same fluid volume thereas to a control group. The administration was carried out every 14 days for all groups (Table 2).

Testing Method:

General symptoms of the animals were observed everyday as a rule. Their body weights were measured every week. In order to evaluate time-dependent change in renal function, blood was collected from the jugular vein under isoflurane anesthesia. Blood cells were counted in EDTA blood, and renal function markers such as Cre and BUN were evaluated in heparinized blood.

Prior to the blood collection, 1) a food intake, 2) a water intake, 3) a urine weight, 4) the amount of protein excreted into urine, 5) the amount of Cre excreted into urine, and 6) urinary precipitates were tested for 24 hours immediately before the blood collection using a metabolic cage. Each animal was transferred to the metabolic cage 3 days before the blood collection and acclimatized thereto. The measurement in the metabolic cage was performed once four weeks. The experimental schedule is shown in FIG. 1.

TABLE 2

| Group | Test substance | Age in weeks at start of administration | Administration route | Dose | The number of animal |
|---|---|---|---|---|---|
| Normal | Saline | 10 | s.c. | Same dose of saline as that of PEGylated fEPO | 1 |
| Normal | PEGylated fEPO | 10 | s.c. | 36.6 µg/kg B.W. | 1 |
| HPK | Saline | 10 | s.c. | Same dose of saline as that of PEGylated fEPO | 1 |
| HPK | PEGylated fEPO | 10 | sc. | 36.6 µg/kg B.W. | 1 |

As shown in FIG. 1, administration and blood collection (blood cell counting using EDTA blood) were performed alternately every other week. In this operation, the body weight was certainly measured, and general conditions of the animal were observed. The day of the first dose was defined as 0 w. Preliminary data was collected 1 week before the start of administration (−1 w). Subsequently, the experiment was continued until 19 w in such a way of blood collection on 1 w, administration on 2 w, blood collection on 3 w, and administration on 4 w. Collection of heparinized plasma and measurement using a metabolic cage were carried out once per two blood collection runs, i.e., once every four weeks.

(Results)

For the experiment, it was difficult to ensure a large number of HPK rats. Hence, the experiment was conducted using one rat per group of PEGylated fEPO and a vehicle. HPK had a body weight smaller than the normal, and the HPK rat given saline exhibited more gradual increase in body weight compared with HPK rat given the PEGylated fEPO (FIG. 2A).

Figure 2B:
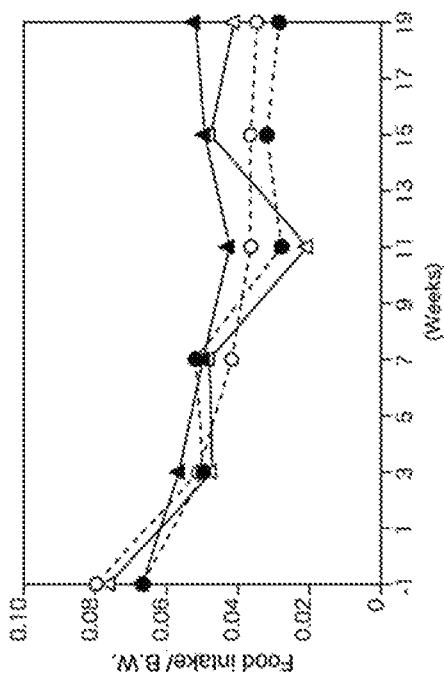
FIGS. 2A to 2D are graphs showing physiological data on an animal in an experimental period in Test 1.
Figure 2D:
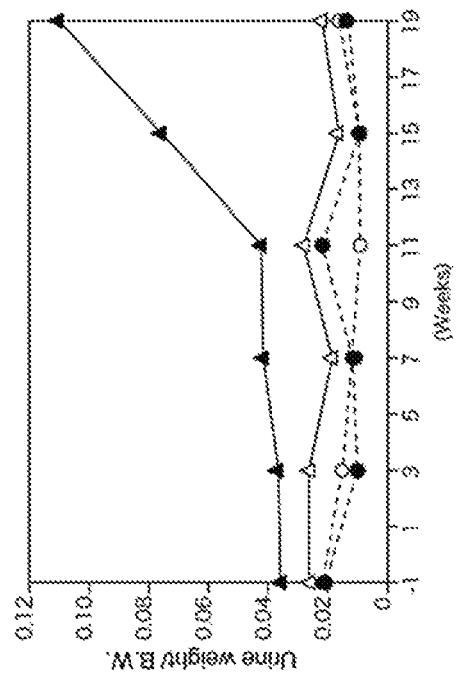
Figure 2A:
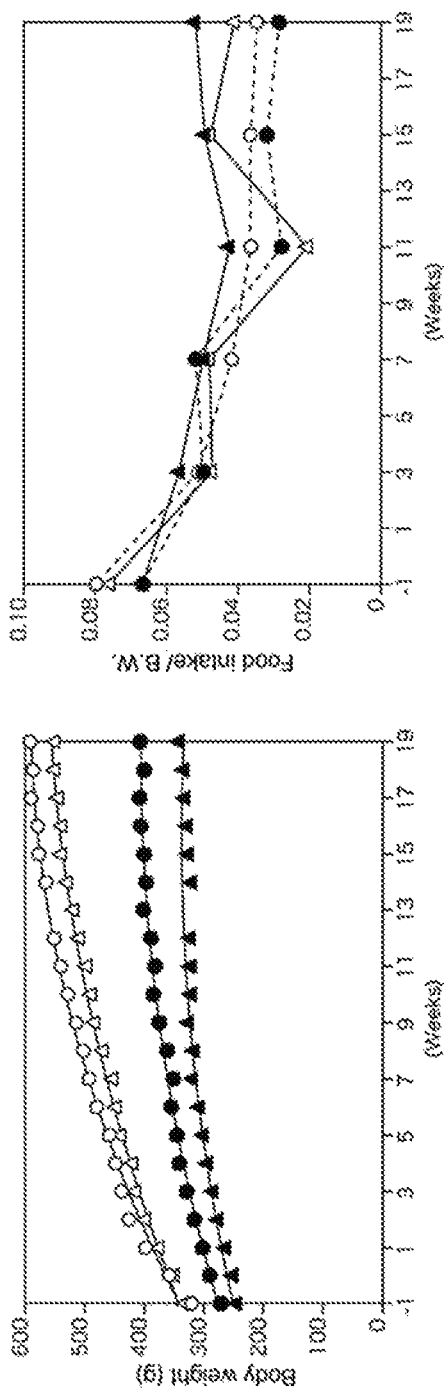
Figure 2C:
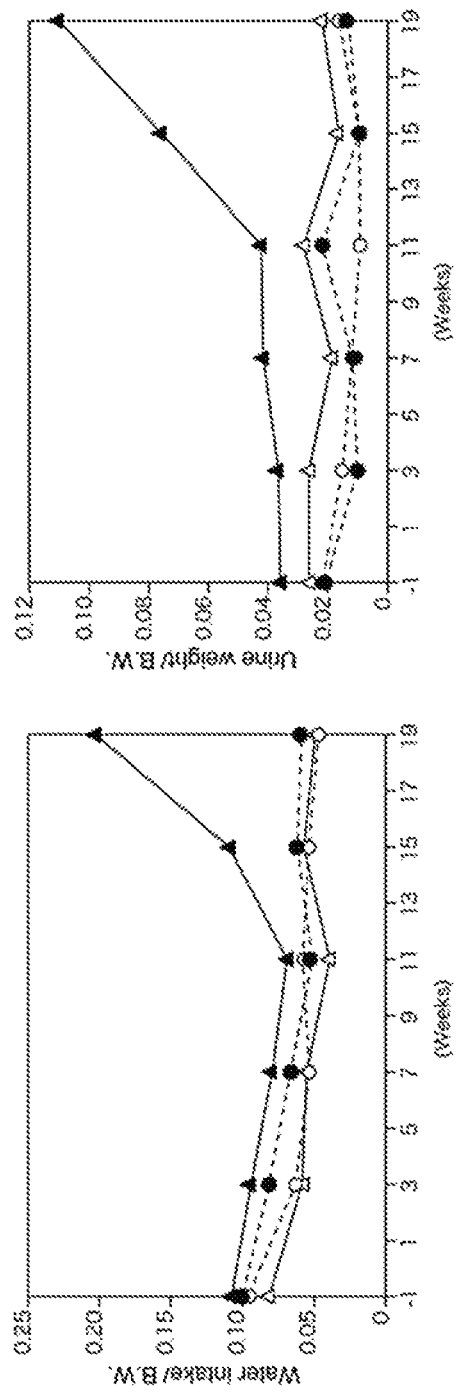

Change in food intake was found to be free from influence dependent on genotype and the presence or absence of administration (FIG. 2B). The water intake and the urine weight in HPK rat given saline were increased on and after 11 weeks, whereas it appeared that the administration of the PEGylated fEPO inhibited increase in water intake and urine weight (FIGS. 2C and 2D).

In the hematological examination, continuous increase in red blood cell count was observed in the normal individual given EPO, whereas no evident increase in hematopoiesis was observed in HPK rat given EPO (FIG. 2E).

BUN and plasma Cre exhibited an upward tendency in the HPK rat given saline, where the administration of the PEGylated fEPO reduced such elevation to some extent (FIGS. 2F and 2G).

(Discussion)

Since HPK rats manifest dilute urine, polydipsia/polyuria found in the HPK rats is ascribable to defect in tubular concentration, which is probably due to failure in tubular absorption of water in response to a high filtration status by individual swollen nephrons. Increase in leaky protein level or interstitial fibrosis ascribable to glomerular barrier disorder, which gets more severe with advancing age in day, might further deteriorate the defect in tubular absorption. However, the urine weight was maintained at a relatively low level by the administration of the PEGylated fEPO, suggesting that the progression of these pathological abnormalities was partially inhibited.

Previous pathological analysis on HPK rats shows that 70-day-old or older HPK rats exhibit deteriorated renal dysfunction and gradually elevated BUN or plasma Cre and manifest more severe polydipsia/polyuria or albuminuria, more severe hypoalbuminemia, hyperlipemia, hypertension, or renal anemia, hyperparathyreoidismus, etc. In this experiment, BUN and plasma Cre rose in the HPK rat given saline, and deterioration in the excreting ability of the kidney, which is consistent with the previous reports, was confirmed to occur in the HPK rat. However, the administration of the PEGylated fEPO reduced elevation in BUN or plasma Cre, suggesting that the deterioration in the excreting ability of the kidney, i.e., reduction in glomerular filtration rate, was partially alleviated.

<Test 2: Long-Term Administration of PEGylated fEPO Chronic Kidney Disease Model Rat>

A test was conducted to administer PEGylated fEPO to a male HPK rat and a male normal rat until 11 weeks old after the start of the test by the same procedures as in Test 1 except that a test group given the PEGylated fEPO at a dose of 73.2 µg/kg body weight was added to the test.

Figure 3A:
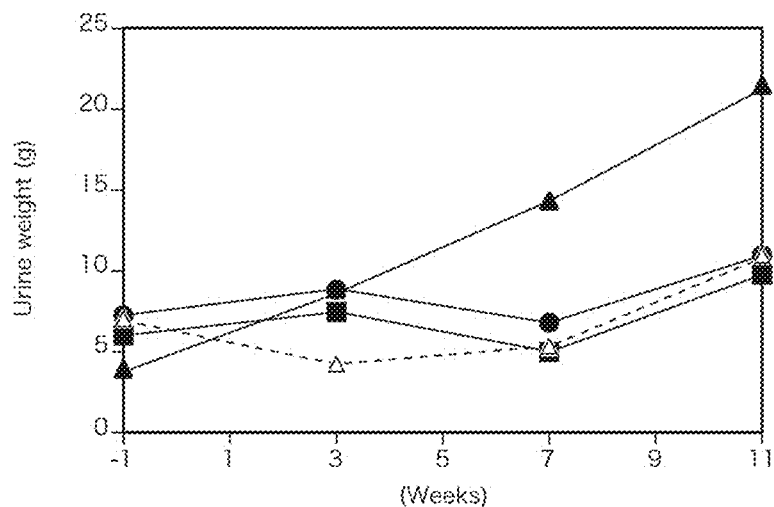
FIGS. 3A to 3C are graphs showing change in urine weight (FIG. 3A), blood urea nitrogen (BUN) (FIG. 3B), and creatinine (Cre) concentration (FIG. 3C) of an animal in an experimental period in Test 2. PEGylated fEPO was administered on 0, 4, 6, 8, and 10 weeks.
Figure 3B:
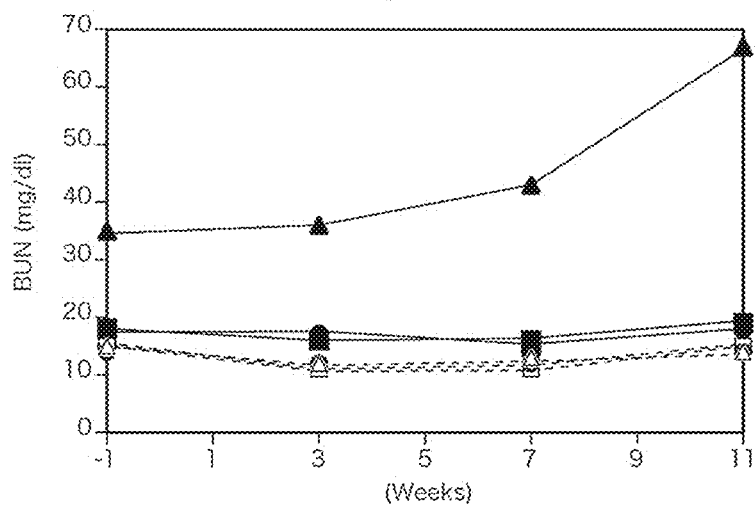
Figure 3C:
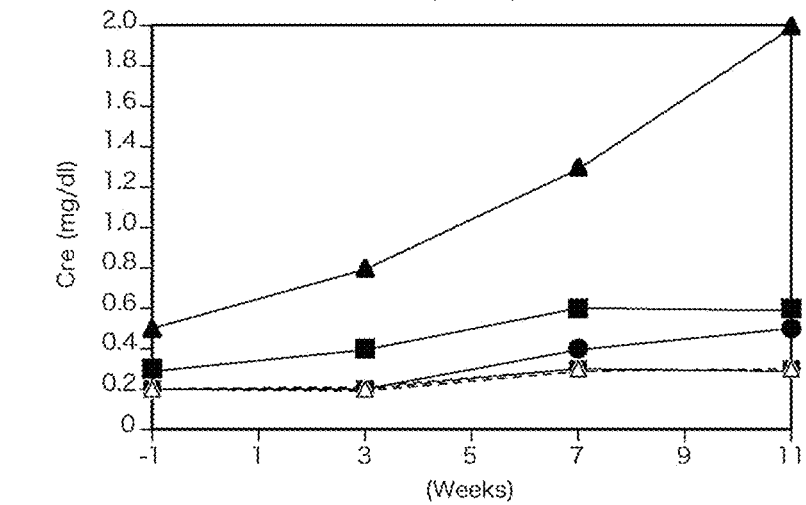

Results of measuring a urine weight, BUN, and plasma Cre are shown in FIGS. 3A, 3B, and 3C, respectively. As in Test 1, the wine weight was increased over time in HPK rat given saline, whereas the administration of the PEGylated fEPO inhibited increase in urine weight (FIG. 3A). Also, BUN and plasma Cre exhibited an upward tendency in the HPK rat given saline, whereas the administration of the PEGylated fEPO was able to reduce elevation in these levels (FIGS. 3B and 3C).

<Test 3: Pharmacokinetic Test of PEGylated fEPO in Cat>

(Object)

An object of this test is to examine change in radioactivity concentration in plasma when [$^{125}$I]PEGylated fEPO is subcutaneously administered singly to a male cat.

(Experimental Operation)

The [$^{125}$I]PEGylated fEPO was obtained by labeling the PEGylated fEPO prepared by the procedures of the Preparation Example with $^{125}$I by a routine method. The prepared [$^{125}$I]PEGylated fEPO had specific radioactivity of 98.7 MBq/mL.

One cat (strain: Narc: Catus, male) that was 10 months old and had a body weight of 3.6 kg at the time of administration was used as a test animal. The [$^{125}$I]PEGylated fEPO was subcutaneously administered singly at a dose of 73.2 µg (10.3 Mbq)/0.8 mL/kg body weight to the neck and the back of this cat under fasting using a polypropylene syringe equipped with a stainless injection needle.

After the single subcutaneous administration of the [$^{125}$I] PEGylated fEPO, blood was collected at the points in time of 0.5, 1, 24, 96, 168, 336, 504, and 672 hours after the administration.

Plasma was prepared from the collected blood and dispensed into containers for radioactivity measurement, followed by the measurement of radioactivity.

The radioactivity measurement was performed using a gamma counter. The plasma radioactivity concentration (ng equiv./mL) was calculated from the measured radioactivity concentration (cpm/mL) in the plasma and the specific radioactivity (cpm/ng) of the [$^{125}$I]PEGylated fEPO.

(Results)

Figure 4:
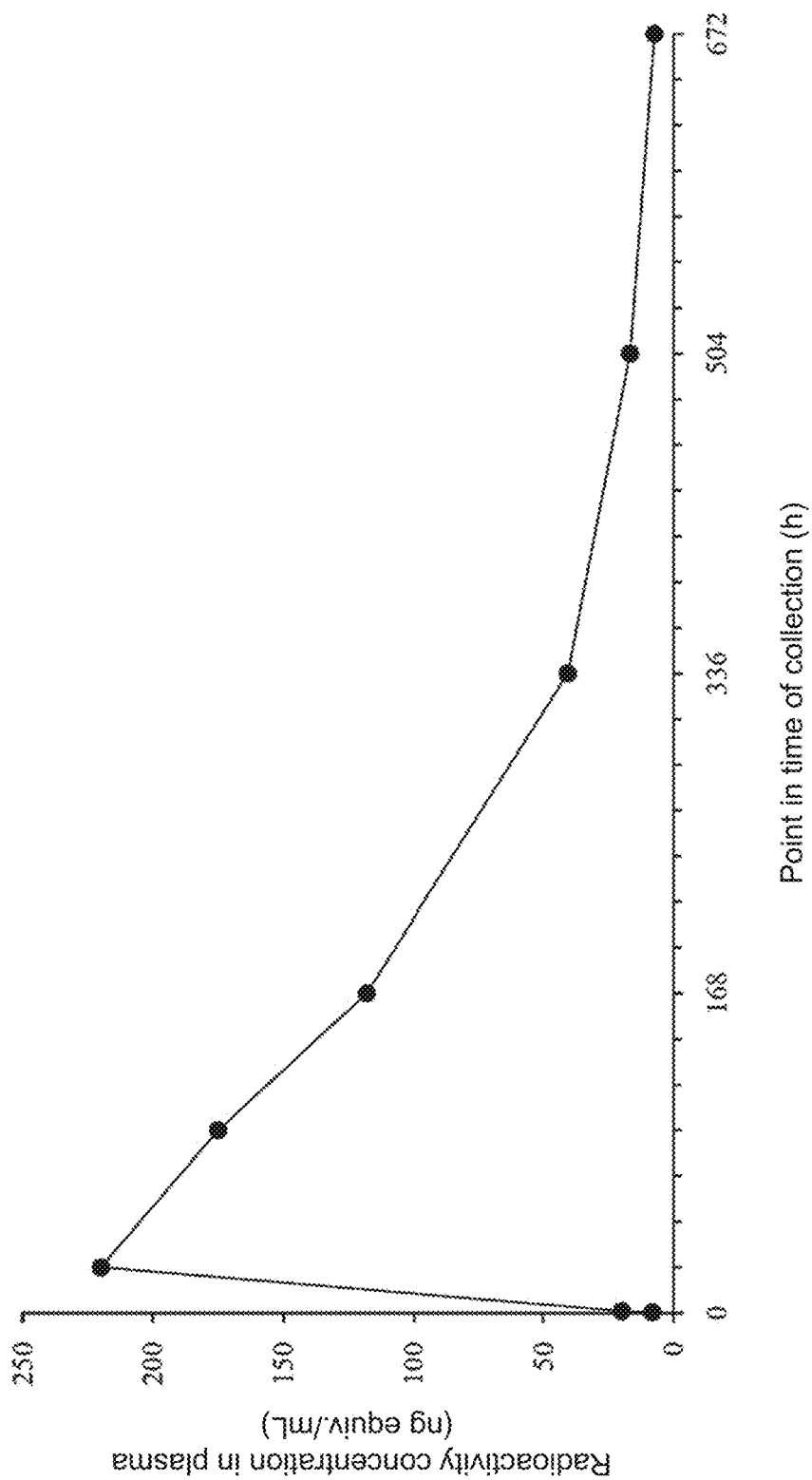
FIG. 4 is a graph showing change in radioactivity concentration in plasma when [$^{125}$I]PEGylated fEPO was subcutaneously administered singly at a dose of 73.2 μg/kg (10.3 Mbq) to a male cat in Test 3.

FIG. 4 shows the radioactivity concentration in plasma when the [$^{125}$I]PEGylated fEPO was subcutaneously administered singly at a dose of 73.2 µg (10.3 Mbq)/kg body weight to the male cat, and the time course thereof.

The radioactivity concentration in plasma when the [$^{125}$I] MEGylated fEPO was subcutaneously administered singly exhibited the highest value 24 hours after the administration (220 ng equiv./mL). Then, the concentration in plasma was gradually decreased and was 118 ng equiv./mL 168 hours after the administration and 7.36 ng equiv./mL 672 hours after the administration. The elimination half-life from 336 to 672 hours after the administration was approximately 136 hours.

These results indicated that the PEGylated fEPO was maintained in blood for approximately 1 month after administration. As is evident from this, the PEGylated fEPO can sustain pharmaceutical efficacy for approximately 1 month after administration.

<Test 4: Safety Evaluation of PEGylated fEPO Continuously Administered for 3 Months to Healthy Cat>

(Object)

An object of this Test 4 is to evaluate safety by the administration of PEGylated fEPO at repeated doses of 36.6 µg/kg or 73.2 µg/kg to a healthy cat.

(Test System)

Test animal: 8 healthy cats (2 to 5 years old, male), n=3 for each group given the PEGylated fEPO. n=4 for a control group given a vehicle.

Test substance: PEGylated fEPO obtained by the same procedures as in the Preparation Example, or a vehicle (buffer aqueous solution having the composition shown in Table 1 except that no PEGylated fEPO was contained)

Dose: 36.6 and 73.2 µg/kg body weight in terms of PEGylated fEPO

Dosing frequency and period: administered once seven days for 3 months (12-time administration)

Sampling point: 5 days after each administration

Evaluation item*: Blood cell count, reticulocyte count, blood biochemistry, iron, neutralizing antibody, body weight

*Blood testing item

General peripheral blood
Reticulocyte count
Total iron binding capacity (TIBC), unsaturated iron binding capacity (UIBC)
Total protein (TP), serum albumin (Alb), albumin/globulin ratio (A/G ratio), blood urea nitrogen (BUN), creatinine (Cre), triglyceride (TG), total cholesterol (T-CHO), lactic dehydrogenase (LDH), creatine phosphokinase (CPK), glutamic pyruvic transaminase (GPT), glutamic oxaloacetic transaminase (GOT), alkaline phosphatase (ALP), calcium (Ca), phosphate (P), serum iron (Fe), gamma glutamine transpeptidase (γ-GTP), serum amyloid A (SAA)

(Hematological Examination (Marker for Effectiveness/ Pharmaceutical Efficacy))

In both the groups given the PEGylated fEPO at a dose of 36.6 µg/kg or 73.2 µg/kg, increase in reticulocyte count, red blood cell count, hematocrit level, and hemoglobin concentration was observed from the start of the administration. The change in these factors was probably change ascribable to the administration of the PEGylated fEPO.

Figure 5A:
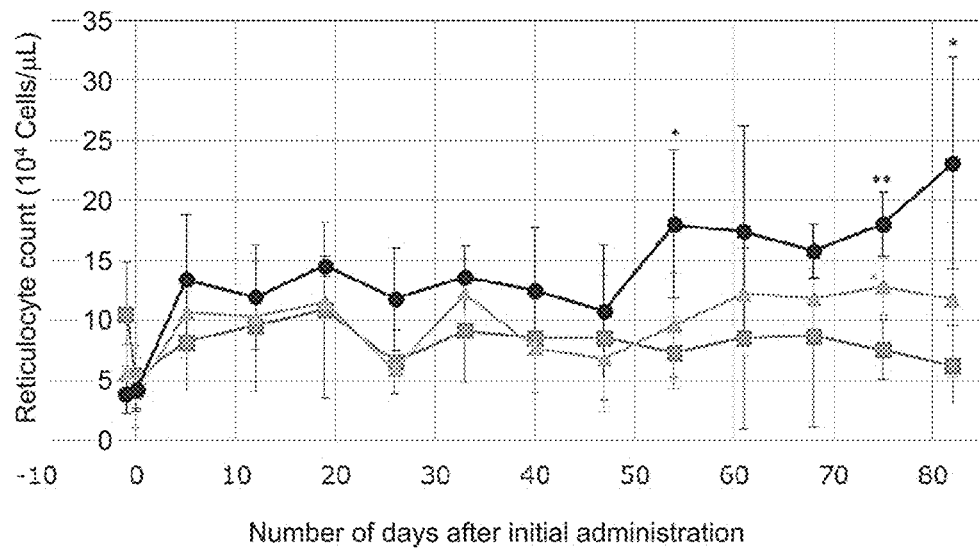
FIGS. 5A and 5B show change in average values of reticulocyte count (FIG. 5A) and red blood cell count (FIG. 5B) in each group in Test 4.

FIG. 5A shows change in the average value of the reticulocyte count in each group vs. the number of days from the initial administration. In the vehicle administration group (control group), no change caused by the vehicle administration was observed, though increase and decrease were repeated as compared with the value before the administration. In the PEGylated fEPO administration groups, the average value was increased with repeated increase and decrease during the testing period, and significant difference was observed 75 days after the administration in the 36.6 µg/kg administration group and 54, 75 and 82 days after the administration in the 73.2 µg/kg administration group.

Figure 5B:
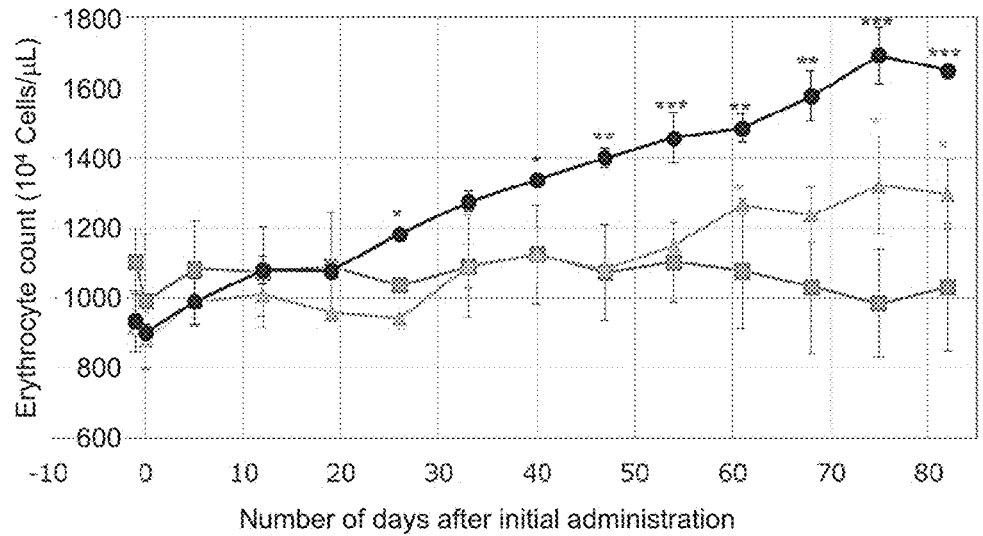

FIG. 5B shows change in the average value of the red blood cell count in each group vs. the number of days from the initial administration. In the vehicle administration group, no change caused by the vehicle administration was observed, though increase and decrease were repeated as compared with the value before the administration. In the PEGylated fEPO administration groups, the average value was increased with repeated increase and decrease during the testing period, and significant difference was observed 61, 75 and 82 days after the administration in the 36.6 µg/kg administration group and 26, 40, 47, 54, 61, 68, 75 and 82 days after the administration in the 73.2 µg/kg administration group.

Although rapid decrease in Fe level was observed from the start of administration through the 5th day in both the PEGylated fEPO administration groups, the Fe level hovered at the lower level value in the normal range during the testing period. Increase in TIBC and UIBC was observed after the initial administration in both the PEGylated fEPO administration groups. Change in these factors was probably change ascribable to the administration of the PEGylated fEPO.

Furthermore, decrease in mean corpuscular volume (MCV) and mean corpuscular hemoglobin (MCH) was observed from the start of administration in both the PEGylated fEPO administration groups. Change in these factors was probably change ascribable to the administration of the PEGylated fEPO. No abnormality was found in mean corpuscular hemoglobin concentration (MCHC) and white blood cells (WBC) throughout the testing period in all the animals.

(Change in Body Weight (Marker for Safety))

No influence of the administration of the PEGylated fEPO was found in body weight throughout the testing period in all the individuals.

(Biochemical Examination of Blood (Marker for Safety))

No influence of the administration of the PEGylated fEPO was found in TG, SAA, TP, Alb, Ca, P, BUN, Cre, GOT, GPT, LDH, CPK, ALP, γ-GTP and T-CHO throughout the testing period in all the control group, the PEGylated fEPO 36.6 µg/kg administration group, and the PEGylated fEPO 73.2 µg/kg administration group, though their values in some individuals transiently departed from the normal levels.

(Conclusion of Test 4)

As is evident from these results, the repeated doses of the PEGylated fEPO for 3 months to healthy cats have no safety problem.

<Test 5: Confirmation of Dose Dependency of Pharmaceutical Efficacy of PEGylated fEPO>

(Object)

The putative dose of PEGylated fEPO for inhibiting chronic kidney disease in cats is 36.6 µg/kg body weight or 73.2 µg/kg body weight. Accordingly, an object of this Test 5 is to evaluate safety by administering PEGylated fEPO in excess of the putative dose to a cat and comparing pharmaceutical efficacy, as a safety test.

(Method)

Test animal: healthy cat (3 to 4 years old, male)

Test substance: PEGylated fEPO obtained by the same procedures as in the Preparation Example, or a vehicle (buffer aqueous solution having the composition shown in Table 1 except that no PEGylated fEPO was contained)

Dose: single administration of 36.6, 73.2, 219.6, and 366.0 µg/kg body weight in terms of PEGylated fEPO Evaluation point: before the administration, blood collection every day for 1 week after the administration, subsequent blood collection every other day, which was continued for approximately 45 days after the administration (until the reticulocyte count returned to the baseline)

Evaluation item: reticulocyte count (Test Group)

Eight cat individuals were identified with individual numbers. The body weight of each individual and the dose of the PEGylated fEPO thereto are as described in the following table.

TABLE 3

| Individual number | Body weight (kg) | PEGylated fEPO dose (µg/kg) |
|---|---|---|
| 1 | 4.99 | 36.6 |
| 2 | 4.96 | 36.6 |
| 3 | 3.82 | 73.2 |
| 4 | 5.27 | 73.2 |
| 8 | 3.97 | 219.6 |
| 9 | 3.27 | 219.6 |
| 11 | 4.59 | 366.0 |
| 12 | 3.37 | 366.0 |

(Results)

Figure 6:
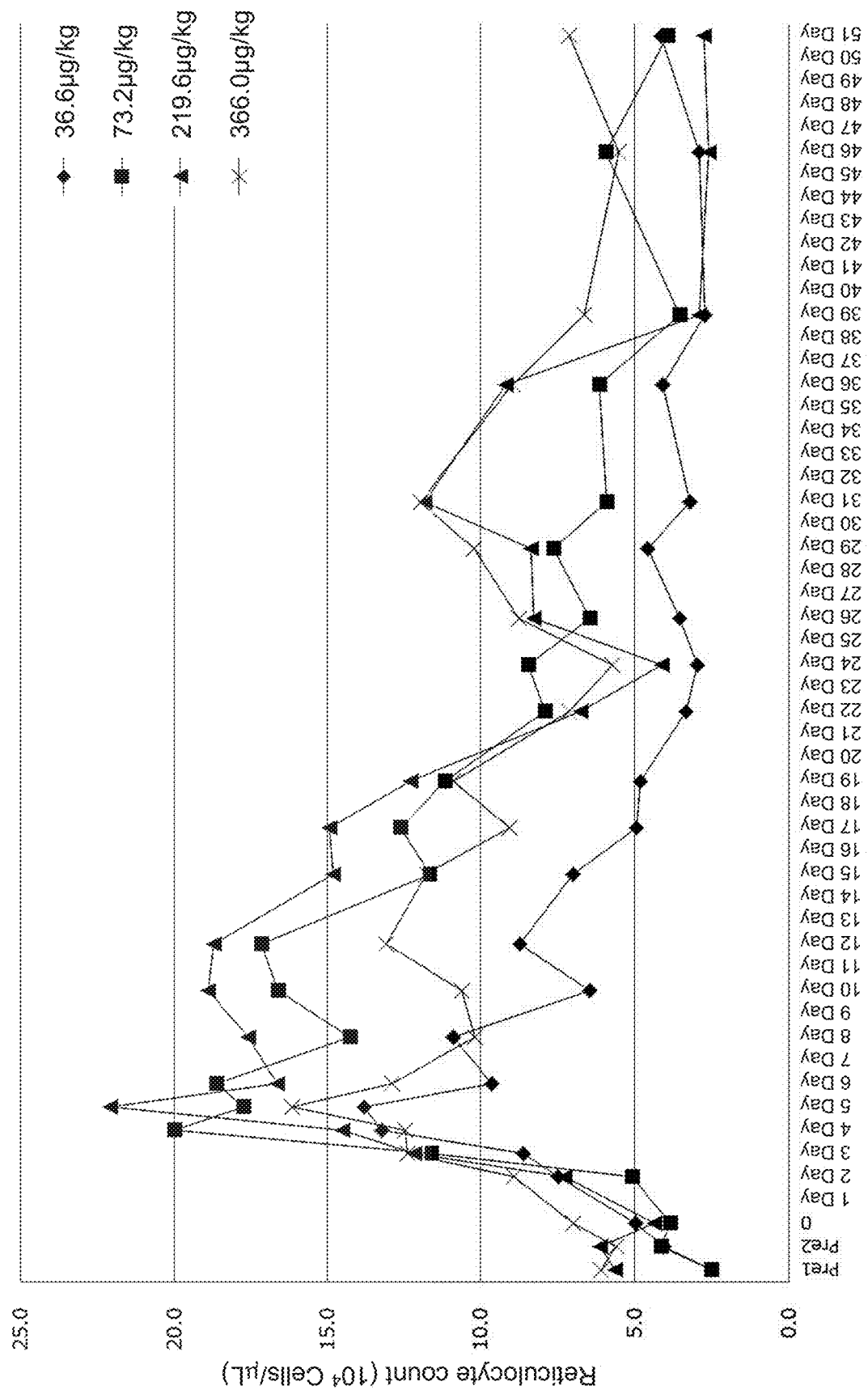
FIG. 6 is a graph showing change in reticulocyte count when PEGylated fEPO was subcutaneously administered singly at any of four doses to a healthy cat in Test 5. An average value of each dose group is shown (n=2).

FIG. 6 shows the results of measuring the reticulocyte count as an average value in each PEGylated fEPO dose group.

The peak of pharmaceutical efficacy was 4 to 5 days after the administration without depending on the dose.

Furthermore, any adverse reaction such as anaphylactic shock was not observed, in spite of the fact that each individual was an individual that actually underwent the administration of PEGylated fEPO a plurality of times in the past.

All publications, patents and patent applications cited herein are incorporated herein by reference in their entirety.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. A method for inhibiting renal hypofunction in a non-human mammal, the method comprising administering cat-derived erythropoietin to the non-human mammal,
wherein the administration of the cat-derived erythropoietin inhibits elevation in creatinine concentration in blood and/or elevation in blood urea nitrogen concentration in the non-human mammal,
wherein the non-human mammal is a non-human mammal having chronic kidney disease without anemia during the administration,
wherein the cat-derived erythropoietin comprises an amino acid sequence selected from the group consisting of SEQ ID NO: 2, SEQ ID NO: 3, an active mutant of SEQ ID NO: 2, and an active mutant of SEQ ID NO: 3,
wherein the active mutant of SEQ ID NO: 2 is an amino acid sequence having 97% or more amino acid identity to SEQ ID NO: 2 and is derived from SEQ ID NO: 2 by addition, deletion, and/or substitution of one or more amino acids, and exhibits at least 60% of erythropoietin activity of the polypeptide consisting of SEQ ID NO: 2,
wherein the active mutant of SEQ ID NO: 3 is an amino acid sequence having 97% or more amino acid identity to SEQ ID NO: 3 and is derived from SEQ ID NO: 3 by addition, deletion, and/or substitution of one or more amino acids, and exhibits at least 60% of erythropoietin activity of the polypeptide consisting of SEQ ID NO: 3,
wherein the cat-derived erythropoietin is chemically modified with polyethylene glycol (PEG),
wherein the chronic kidney disease is classified into chronic kidney disease stage I or stage II defined by the International Renal Interest Society at least at the start of the administration,
wherein a weight-average molecular weight of the PEG is 5 to 40 kDa, and
wherein administering the cat-derived erythropoietin is performed repeatedly at a time interval of 7 or more days.

2. The method according to claim 1, wherein the non-human mammal has the chronic kidney disease and the renal hypofunction is caused by the chronic kidney disease.

3. The method according to claim 1, wherein administering the cat-derived erythropoietin is performed repeatedly at a time interval of 7 to 30 days.

4. The method according to claim 3, wherein a dose of the erythropoietin for each administration is 3 to 400 µg/kg body weight.

5. The method according to claim 1, wherein the non-human mammal has a creatinine concentration in blood of 2.7 mg/dL or lower at least at the start of the administration.

6. The method according to claim 1, further comprising at least one selected from the group consisting of:
administering an iron supplement to the non-human mammal;
administering intravenous fluids to the non-human mammal;
subjecting the non-human mammal to dialysis;
subjecting the non-human mammal to diet therapy;
administering an antihypertensive agent to the non-human mammal;
administering an adsorbent to the non-human mammal;
administering vitamin to the non-human mammal; and
administering a diuretic to the non-human mammal.

7. The method according to claim 1, wherein the cat-derived erythropoietin comprises the amino acid sequence of SEQ ID NO: 2 or the amino acid sequence of SEQ ID NO: 3.

8. The method according to claim 1, wherein the active mutant of SEQ ID NO: 2 is derived from SEQ ID NO: 2 by addition, deletion, and/or substitution of 1 or 2 amino acids, and the active mutant of SEQ ID NO: 3 is derived from SEQ ID NO: 3 by addition, deletion, and/or substitution of 1 or 2 amino acids.

9. The method according to claim 1, wherein administering the cat-derived erythropoietin is performed repeatedly at a time interval of 8 or more days.

10. A method for inhibiting renal hypofunction in a non-human mammal, the method comprising administering cat-derived erythropoietin to the non-human mammal,
wherein the administration of the cat-derived erythropoietin inhibits elevation in creatinine concentration in blood and/or elevation in blood urea nitrogen concentration in the non-human mammal,
wherein the non-human mammal is a non-human mammal having chronic kidney disease without anemia during the administration,
wherein the cat-derived erythropoietin comprises an amino acid sequence selected from the group consisting of SEQ ID NO: 2, SEQ ID NO: 3, an active mutant of SEQ ID NO: 2 derived from SEQ ID NO: 2 by addition, deletion, and/or substitution of a total 1 to 5 amino acids, and an active mutant of SEQ ID NO: 3 derived from SEQ ID NO: 3 by addition, deletion, and/or substitution of a total 1 to 4 amino acids,
wherein the cat-derived erythropoietin is chemically modified with polyethylene glycol (PEG),
wherein the chronic kidney disease is classified into chronic kidney disease stage I or stage II defined by the International Renal Interest Society at least at the start of the administration,
wherein a weight-average molecular weight of the PEG is 5 to 40 kDa, and
wherein administering the cat-derived erythropoietin is performed repeatedly at a time interval of 7 or more days.

11. The method according to claim 10, wherein the active mutant of SEQ ID NO: 2 is derived from SEQ ID NO: 2 by addition, deletion, and/or substitution of 1 or 2 amino acids, and the active mutant of SEQ ID NO: 3 is derived from SEQ ID NO: 3 by addition, deletion, and/or substitution of 1 or 2 amino acids.

12. The method according to claim 10, wherein the cat-derived erythropoietin comprises the amino acid sequence of SEQ ID NO: 2 or the amino acid sequence of SEQ ID NO: 3.

13. The method according to claim 10, wherein administering the cat-derived erythropoietin is performed repeatedly at a time interval of 8 or more days.

* * * * *

SEQUENCE LISTING

```
<160> NUMBER OF SEQ ID NOS: 3

<210> SEQ ID NO 1
<211> LENGTH: 579
<212> TYPE: DNA
<213> ORGANISM: Felis catus

<400> SEQUENCE: 1
atggggtcgt gcgaatgtcc tgccctgctg cttctgctat ctttgctgct gcttcccctg      60
ggcctcccag tcctgggcgc cccccctcgc ctcatctgtg acagccgagt cctggagagg     120
tacattctgg aggccaggga ggccgaaaat gtcacgatgg gctgtgctga aggctgcagc     180
ttcagtgaga atatcactgt cccagacacc aaggtcaact tctatacctg gaagaggatg     240
gacgtcgggc agcaggctgt ggaagtctgg cagggcctcg ccctgctctc agaagccatc     300
ctgcggggcc aggccctgct ggccaactcc tcccagccat ctgagaccct gcagctgcat     360
gtggataaag ccgtcagcag cctgcgcagc ctcacctccc tgcttcgggc actgggagcc     420
cggaaggaag ccacctccct tccagaggca acctctgctg ctccactccg aacattcact     480
gtcgatactt tgtgcaaact tttccgaatc tactccaact tcctgcgggg aaagctgacg     540
ctgtacacag gggaggcctg ccgaagagga gacaggtga                            579

<210> SEQ ID NO 2
<211> LENGTH: 192
<212> TYPE: PRT
<213> ORGANISM: Felis catus
```

<400> SEQUENCE: 2

Met Gly Ser Cys Glu Cys Pro Ala Leu Leu Leu Leu Ser Leu Leu
1               5                   10                  15

Leu Leu Pro Leu Gly Leu Pro Val Leu Gly Ala Pro Pro Arg Leu Ile
            20                  25                  30

Cys Asp Ser Arg Val Leu Glu Arg Tyr Ile Leu Glu Ala Arg Glu Ala
                35                  40                  45

Glu Asn Val Thr Met Gly Cys Ala Glu Gly Cys Ser Phe Ser Glu Asn
    50                  55                  60

Ile Thr Val Pro Asp Thr Lys Val Asn Phe Tyr Thr Trp Lys Arg Met
65                  70                  75                  80

Asp Val Gly Gln Gln Ala Val Glu Val Trp Gln Gly Leu Ala Leu Leu
                85                  90                  95

Ser Glu Ala Ile Leu Arg Gly Gln Ala Leu Leu Ala Asn Ser Ser Gln
                100                 105                 110

Pro Ser Glu Thr Leu Gln Leu His Val Asp Lys Ala Val Ser Ser Leu
            115                 120                 125

Arg Ser Leu Thr Ser Leu Leu Arg Ala Leu Gly Ala Arg Lys Glu Ala
        130                 135                 140

Thr Ser Leu Pro Glu Ala Thr Ser Ala Ala Pro Leu Arg Thr Phe Thr
145                 150                 155                 160

Val Asp Thr Leu Cys Lys Leu Phe Arg Ile Tyr Ser Asn Phe Leu Arg
                165                 170                 175

Gly Lys Leu Thr Leu Tyr Thr Gly Glu Ala Cys Arg Arg Gly Asp Arg
            180                 185                 190

<210> SEQ ID NO 3
<211> LENGTH: 165
<212> TYPE: PRT
<213> ORGANISM: Felis catus

<400> SEQUENCE: 3

Ala Pro Pro Arg Leu Ile Cys Asp Ser Arg Val Leu Glu Arg Tyr Ile
1               5                   10                  15

Leu Glu Ala Arg Glu Ala Glu Asn Val Thr Met Gly Cys Ala Glu Gly
            20                  25                  30

Cys Ser Phe Ser Glu Asn Ile Thr Val Pro Asp Thr Lys Val Asn Phe
        35                  40                  45

Tyr Thr Trp Lys Arg Met Asp Val Gly Gln Gln Ala Val Glu Val Trp
    50                  55                  60

Gln Gly Leu Ala Leu Leu Ser Glu Ala Ile Leu Arg Gly Gln Ala Leu
65                  70                  75                  80

Leu Ala Asn Ser Ser Gln Pro Ser Glu Thr Leu Gln Leu His Val Asp
                85                  90                  95

Lys Ala Val Ser Ser Leu Arg Ser Leu Thr Ser Leu Leu Arg Ala Leu
                100                 105                 110

Gly Ala Arg Lys Glu Ala Thr Ser Leu Pro Glu Ala Thr Ser Ala Ala
            115                 120                 125

Pro Leu Arg Thr Phe Thr Val Asp Thr Leu Cys Lys Leu Phe Arg Ile
        130                 135                 140

Tyr Ser Asn Phe Leu Arg Gly Lys Leu Thr Leu Tyr Thr Gly Glu Ala
145                 150                 155                 160

Cys Arg Arg Gly Asp
            165